US012260956B2

(12) United States Patent
Morcillo Montejo et al.

(10) Patent No.: US 12,260,956 B2
(45) Date of Patent: Mar. 25, 2025

(54) HEALTHCARE DATA MANAGEMENT SYSTEM

(71) Applicant: Roche Diagnostics Operations, Inc., Indianapolis, IN (US)

(72) Inventors: Alejandro Morcillo Montejo, Sant Cugat del Vallès (ES); Raúl Ropero Ruíz, Rubi (ES)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 191 days.

(21) Appl. No.: 18/063,836

(22) Filed: Dec. 9, 2022

(65) Prior Publication Data

US 2023/0187066 A1    Jun. 15, 2023

(51) Int. Cl.
G16H 40/67 (2018.01)
H04L 9/40 (2022.01)

(52) U.S. Cl.
CPC .......... G16H 40/67 (2018.01); H04L 63/101 (2013.01); H04L 63/102 (2013.01)

(58) Field of Classification Search
CPC ...... G16H 40/67; H04L 63/101; H04L 63/102
USPC ........................................................ 707/792
See application file for complete search history.

(56) References Cited

U.S. PATENT DOCUMENTS

| | | | |
|---|---|---|---|
| 7,689,438 B1 * | 3/2010 | Rappaport | G16H 40/67 600/300 |
| 9,785,792 B2 | 10/2017 | Barrett et al. | |
| 11,087,878 B2 * | 8/2021 | Vesto | G16H 50/50 |

(Continued)

FOREIGN PATENT DOCUMENTS

| | | |
|---|---|---|
| CN | 109257415 | 1/2019 |
| KR | 20200127814 | 11/2020 |

OTHER PUBLICATIONS

Nguyen, Dinh C., et al., "Blockchain for Secure EHRs Sharing of Mobile Cloud Based E-Health Systems", IEEE Access, vol. 7, May 17, 2019, pp. 66792-66806.*

(Continued)

*Primary Examiner* — Robert Stevens
(74) *Attorney, Agent, or Firm* — Lee & Hayes, P.C.

(57) ABSTRACT

A healthcare data management system for managing healthcare data comprising in-vitro diagnostics (IVD) data created using at least one IVD analytical instrument, the healthcare data management system being accessible by a plurality of client devices. The healthcare data management system including: a plurality of healthcare applications each configured to execute one or more operations associated with the healthcare data management system using healthcare data of the healthcare data management system; an intent management system including: an intent registry, storing information about a plurality of intents, the information for each intent including: an intent type identifier, and one or more healthcare applications configured to execute an operation associated with the intent type; and the intent management system further comprising: a healthcare application determination module configured to receive an intent, and to determine, using the intent registry, one or more healthcare applications configured to execute an operation associated with the received intent.

20 Claims, 13 Drawing Sheets

(56) References Cited

U.S. PATENT DOCUMENTS

| | | | | |
|---|---|---|---|---|
| 2011/0307274 | A1* | 12/2011 | Thompson | G16H 10/60 |
| | | | | 717/173 |
| 2015/0095066 | A1* | 4/2015 | Ryan | G06Q 50/22 |
| | | | | 705/3 |
| 2015/0363555 | A1* | 12/2015 | Studsrud | G16H 40/20 |
| | | | | 705/2 |
| 2016/0055300 | A1* | 2/2016 | Ganesh | G16H 10/60 |
| | | | | 705/3 |
| 2017/0032091 | A1 | 2/2017 | Rudorfer et al. | |
| 2017/0109478 | A1* | 4/2017 | Hasan | G16H 50/20 |
| 2018/0121857 | A1* | 5/2018 | Gutman | G16H 15/00 |
| 2018/0150599 | A1* | 5/2018 | Valdes | G06F 16/904 |
| 2019/0096533 | A1 | 3/2019 | Ramaci | |
| 2020/0356353 | A1* | 11/2020 | Jain | H04L 67/125 |
| 2022/0038430 | A1* | 2/2022 | Fagan | H04L 63/0807 |
| 2022/0391270 | A1* | 12/2022 | Gnanasambandam | |
| | | | | G16H 20/70 |

OTHER PUBLICATIONS

Pace, Pasquale, et al., "An Edge-Based Architecture to Support Efficient Applications for Healthcare Industry 2.0", IEEE Transactions on Industrial Informatics, vol. 15, No. 1, Jan. 2019, pp. 481-489.*

European Search Report issued May 25, 2022, in Application No. 21383144.9, 2 pp.

* cited by examiner

| Intent Type ID | Intent Type | Supporting application IDs |
| --- | --- | --- |
| 1 | OPEN_ORDER | A, B, C |
| 2 | OPEN_PATIENT | A |
| 3 | SEARCH_PATIENT | B, C |
| 4 | SEARCH_DEVICE | B |
| 5 | OPEN_DEVICE | A, B |
| 6 | OPEN_REAGENT_CONSUMPTION | C |

Fig. 3A

| Application ID | Supported intent type IDs |
| --- | --- |
| A | 1, 2, 5 |
| B | 1, 3, 4, 5 |
| C | 1, 3, 6 |

Fig. 3B

| Entity ID | Permitted intent type IDs |
|---|---|
| 0001 | 1, 2, 5 |
| 0002 | 1, 3, 4, 5 |
| 0003 | 1, 3, 6 |

Fig. 6A

| Entity ID | Permitted OPERATION IDs |
|---|---|
| 0001 | 1, 4, 6 |
| 0002 | 1, 2, 4, 5 |
| 0003 | 1, 3, 6 |

Fig. 6B

| Entity ID | Permitted data type IDs |
|---|---|
| 0001 | 1, 2, 5 |
| 0002 | 1, 3, 4, 5 |
| 0003 | 1, 3, 6 |

Fig. 6C

| Entity ID | Permitted data items |
|---|---|
| 0001 | 1, 4, 6 |
| 0002 | 1, 2, 4, 5 |
| 0003 | 1, 3, 6 |

Fig. 6D

| Entity ID | Permitted application IDs |
|---|---|
| 0001 | 1, 2, 5 |
| 0002 | 1, 3, 4, 5 |
| 0003 | 1, 3, 6 |

Fig. 6E

| User ID | 0001 |
|---|---|
| Intent OPERATION ID | A |
| Intent DATA ID | B |
| Intent successful? | Yes |
| Timestamp | 09.06.2021 21:30:55 |

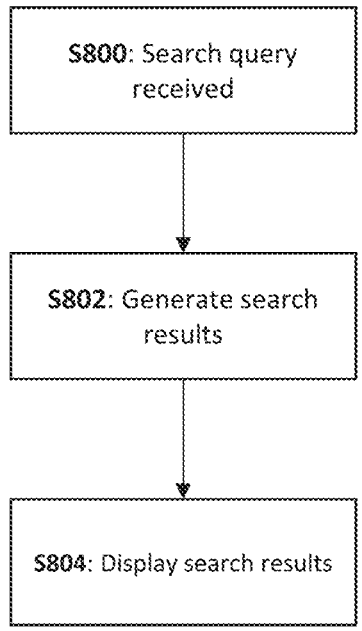
Fig. 9A
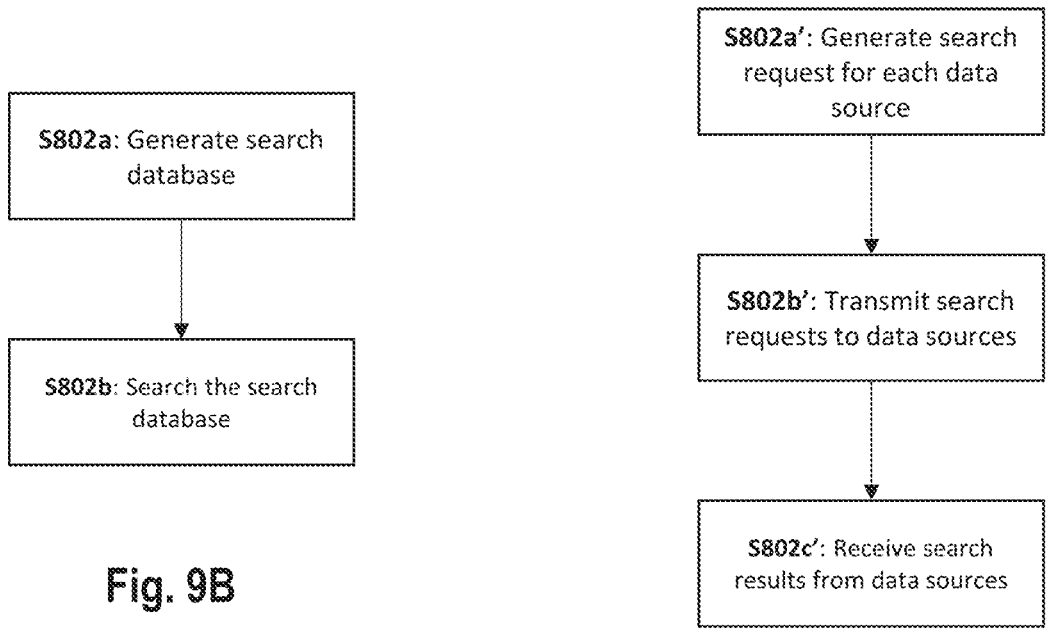
Fig. 9B
Fig. 9C

| Source | Patient Management |
|---|---|
| Date | 20.05.2021 |
| Quality score | 0.68 |
| Match number | 2 |
| INTENTS | <INTENT1><br><INTENT2> |

HEALTHCARE DATA MANAGEMENT SYSTEM

CROSS-REFERENCE TO RELATED APPLICATIONS

This application claims priority to European Patent Application No. 21383144.9 filed Dec. 15, 2021, the disclosure of which is hereby incorporated by reference in its entirety.

TECHNICAL FIELD

The present disclosure relates to a healthcare data management system.

BACKGROUND

Computational ecosystems, and particularly those in the healthcare field, are typically formed of applications which act as a solution or solutions for solving a problem or set of problems that have a relationship amongst them. These applications can be made by the same provider, or multiple providers.

A significant challenge in this kind of ecosystem is the integration of these applications so as to find the right balance for users, whilst avoiding unnecessary coupling of the applications to one another. Additionally, in order to make the integration meaningful, it could be beneficial to adapt to the domain for each user (or persona) according to their specialisation. The present disclosure was arrived at in light of the above considerations.

SUMMARY

In some aspects, the present disclosure provides a system, for example an intent-based (e.g., intended action-based) application management system, for allocating healthcare data management operations among data management applications in which intents (or requests or commands) are analysed to determine intended actions and used to provide effective interfacing between multiple, e.g. all, of the different components (e.g., applications) of the system. For example, intents or intended actions may be determined from user input and, based on the determined intent or intended actions, a lookup in a registry of intended actions with associated data management applications and/or operations is performed to select among the applications and/or operations, and then identified to the user and/or executed. In order to provide an interface between the system itself and the data management applications or operations, applications are stored on or accessible via an application server connected with the system. Based on determining intended actions, the system may also provide an interface or operational relationship between applications for performing the intended actions. In the present disclosure, an intent-based (e.g., intended action-based) application management system is provided which may be accessed by users of client devices. The system effectively provides a portal via which a user can access a plurality of applications which may be hosted at various servers (either local area network, LAN, servers or wide area network, WAN, servers, e.g. the cloud). The intent-based interactions between the various components of the system may be managed by an intent management system which may act as a go-between any two components which wish somehow to interact. At a high level, an intent may be based on a statement which describes an action which a user wishes to perform, but without necessarily specifying the application which is to perform the action (and, typically, without specifying the details of the performance of the action). For example, an intent (e.g., intended action) may be in the form of a simple statement such as "view a map", or "take a picture". The intent "view a map" may specify this without indicating an application to be used to view the map, or any particulars on how the map is to be displayed (e.g. zoom level, etc.). Later in this application, the properties of an intent are explained in more detail. The present disclosure is particularly advantageous in its application to a distributed system, which may be accessed via a portal or platform, and the operations of which are controlled centrally by an intent management system.

The advantageous technical effects of the disclosure may be provided by a system (such as an application management system, a portal, a platform, or another distributed system) which is accessible by a client device, or a user thereof. The system may include a plurality of applications hosted on one or more application servers. The system may include an intent management system, which is configured to receive requests in the form of intents from the client devices or from individual applications, and which is configured to manage those requests, for example by determining which application should execute an operation associated with the intent. In order to do so, the intent management system may include an intent registry, which lists a plurality of intent types, and applications associated therewith. Systems according to the present disclosure may be equipped to perform permissions and consent management, and may be able to track interactions with the system. The intent-based system of the present disclosure is advantageous in that it can be highly scalable. A new application may register the operations which it is capable of performing with the intent registry, whereby the new application can be able to "join" the system, which then provides an effective interface between the new application and other components of the system. In this way, the disclosure may be said to form a foundation for an ecosystem of applications which can evolve and grow with ease, when those applications have registered with the intent registry. The intent management system is subsequently able to control all application-application interactions, for example.

Specifically, a first aspect of the disclosure provides an electronic healthcare data management system for managing electronic healthcare data operations and data comprising in-vitro diagnostics (IVD) data created using at least one IVD analytical instrument, the healthcare data management system being accessible by a plurality of client devices, the system including:

a plurality of healthcare applications, each healthcare application being configured to execute one or more healthcare data operations associated with the healthcare management system using healthcare data of the healthcare data management system;

a healthcare data operations management system including:
  a healthcare data operations registry storing information about a plurality of healthcare data operation types, the information for each healthcare data operation type including: a healthcare data operation type identifier, and the identification of one or more healthcare applications configured to execute an operation associated with the healthcare data operation type;
  a healthcare application determination module configured to receive a request or command, and to determine, based on analysing the request or command and performing a lookup in the healthcare data operations registry, a selection of one or more healthcare applications configured to execute an operation associated with the received request or command. The selection of the one or more healthcare operations may be reported, displayed, and/or executed.

The IVD analytical instrument(s) may be analytical laboratory instruments, and/or analytical point-of-care instruments. The system may include further in-vivo analytical instruments, and/or medical (e.g. diagnostic) measurement instruments.

Another aspect of the disclosure provides a healthcare data management system for managing healthcare data, the healthcare data:

comprising quantitative medical data created using at least one diagnostic measurement method; and/or comprising quantitative medical data created using at least one medical diagnostic instrument;

the healthcare data management system being accessible by a plurality of client devices, the system including:

a plurality of healthcare applications, each healthcare application being configured:

to execute one or more predetermined operations associated with the healthcare management system using healthcare data of the healthcare data management system; and/or derive additional healthcare data using healthcare data of the healthcare data management system;

an intent management system including:

an intent registry storing information about a plurality of intent types, the information for each intent including: an intent type identifier, and one or more healthcare applications configured to execute an operation associated with the intent type;

a healthcare application determination module configured to receive an intent, and to determine, using the intent registry, one or more healthcare applications configured to execute an operation associated with the received intent.

In a further aspect, the disclosure provides an intent-based application management system, accessible by a plurality of client devices, the system including:

one or more application servers hosting a plurality of applications, each application configured to execute one or more predetermined operations;

an intent management system including:

an intent registry, storing information about a plurality of intents, the information for each intent including:

an intent type identifier, and one or more applications configured to execute an operation associated with the intent type;

and the intent management system further comprising:

an application determination module configured to receive an intent, and to determine, using the intent registry, one or more applications configured to execute an operation associated with the received intent.

Herein, healthcare data management system may be understood to refer to, or to include as a part of it, the intent-based application management system of the above aspect as applied in a healthcare data context. The healthcare data management system may have any one, or any combination insofar as they are compatible, of the optional features of the intent-based application management system set out herein.

The intent-based application management system may also be referred to herein as a digital hub, an application portal, an application management portal, an application coordination system, or an application coordination portal, or equivalent.

In some embodiments, the intent-based application management system may be connected to one or more external devices or systems. The external devices and/or systems may be, for example, laboratory instruments, point of care devices, digital instruments, hospital information systems, laboratory information systems, laboratory middleware, electronic medical record systems and the like and the intent management system may be configured to receive data, notifications, or intents, from them.

In some embodiments, the intent-based application management system, and specifically the intent management system, may be configured to sort one or more intents identified by the intent-based application management system. The sorting may be performed, for example, based on: a history of a user of the client device, a history of an organisation of which the user of the client device is a member, a role of a user of the client device, and/or a history of a user comparable to the user of the client device. The sorting may, for example, be implemented using a machine-learning based sorting algorithm trained on real or synthetic data.

"Application server" may refer to a hardware or software entity which is capable of hosting an application e.g. for execution or transfer to another computing device for execution. The application server may include conventional server-type hardware. The application server may be a dedicated server, or may be a virtual server (e.g. as hosted on a cloud computing network) The application server may include a computer (including a laptop computer, desktop computer, or tablet), or a mobile device (including a mobile phone such as a smartphone). In some cases, the client devices themselves may host at least one application of the plurality of applications, and may be considered to represent application servers in that respect. Herein, the term "application" may be understood as a program or piece of software (which may or may not be self-contained) which performs one or more functions. The one or more application servers host a plurality, e.g. two or more, applications. Each application is configured, e.g. contains machine executable code which causes it to, perform or execute one or more predetermined operations (e.g. open file, close file, modify file, display to user, etc.). The applications may be considered as consumers (or indeed producers) of data. The data is typically provided from external devices/systems as discussed above (e.g. laboratory instruments, point of care (POC) devices, or digital instruments).

The data of the healthcare data management system, including data as received from external devices (e.g. hospital information systems, laboratory information systems, laboratory middleware, electronic medical record systems), may include medical data or medically relevant data. The medical data may be qualitative (e.g. provided by a doctor, for example indicating that the patient has symptom A) or quantitative (e.g. provided using a diagnostic measurement instrument, for example a blood glucose value). The medical data or medically relevant data may include demographic data (for example, male, age 42, non-smoker). The data of the healthcare data management system may include instrument data or operating data, for example data referring or relating to the inner functioning of an IVD instrument. For example, the instrument data can include analytical data, pre-analytical data, or post-analytical data. The instrument data may also include point-of-care instrument data, for example temperature of environment data or calibration data.

The intent-based application management system, the application servers, and the intent management system may refer to a specific server, or specific piece or group of software running on one or more servers, the intent management system including the intent registry and the application determination module. The intent registry may be, for example, a database containing entries, the entries denoting a plurality (e.g. more than two) types of intent, and information for each intent including: an intent type identifier (i.e. information which can be used to identify the type of intent), and the one or more applications. The information relating to the one or more applications may be an application identifier, usable to identify an application which is configured to execute the operation associated with the intent type. By client devices, it may be devices which are serviced by or are used in a server-client relationship with the intent-based application management system. For example, the client devices may be laptop computers, desktop computers, tablets, or mobile devices connectable over a network (wireless or wired) to the intent-based application management system.

Generally, herein, reference to a 'module' may be understood as defining a piece or group of software which is or are configured to perform the function denoted.

In this application, the term "intent" takes a meaning which is specific to computing, rather than the non-technical "dictionary definition" of the word. An intent may be understood herein as a data object which describes a specific operation to be executed, or a desired outcome, which may not necessarily specifying the precise means by which application the operation is to be executed, or by which the outcome is to be achieved. Herein, the term "operation" may be understood to refer to technical operations, such as computer processing operations, or physical operations performed by an item of hardware, such as laboratory equipment. This meaning of "intent" differs from the non-technical definition of the term, i.e. the underlying meaning or intention behind a statement.

Herein, the term "data object" may refer to any kind of computer or electronic object. In some cases, the data object may be in the form of a file which may form part or at least a part of a message, the data object may be transferrable between any two components of the intent-based application management system. The information in the intent may be encoded in computer code and/or in a computer programming language (e.g. as supported by the intent-based application management system, the client devices, and/or any component of the intent-based application management system).

An intent may be a data object which describes a specific operation to be executed on or with respect to one or more data items, or which describes a desired outcome of a specific operation when executed on or with respect to one or more data items.

The "data item(s)" may be located within databases. In some cases, the data items may be stored in databases which are associated with specific applications of the plurality of applications. Herein, data item may be understood as an element of data which has a relationship to the intent and to or with which the intent is to be executed. For example, the data item may be a file identifier, or a resource identifier. In some examples, the data items may be or represent medically or clinically relevant data, for example measurements results from a test etc. (e.g. blood glucose level). The data items may be or represent operating or instrument data, for example reagent level, quality control data, etc.

An intent may not specify which application is to execute the operation.

Even though the intent does not specify the application which is to execute the operation, it may include information salient information which enables the application determination module to select one or more appropriate applications. Accordingly, the intent may include the technical requirements to execute the operation or to achieve the desired outcome.

An intent may include a plurality of fields, each field containing a respective datum indicating an aspect of and/or parameter associated with of the operation to be executed.

The fields may include one or more of:

an OPERATION field defining the type of operation to be executed; and a DATA field defining one or more items on which the operation is to be executed.

The OPERATION field may define or represent the "intent type".

As discussed, the intent may be represented in some kind of computer code, which is a component of a message which is transferred between various components of the intent-based application management system. In view of that, it is desirable that the intent-based application management system includes a component which can automatically generate intents based on a client device input.

In some embodiments, the intent-based application management system may be connected to an external operating system (e.g. Android, iOS, Windows, etc.), which may be a client device of the intent-based application management system, which manages intents specific to its respective operation system. In such examples, the intent-based application management system, and specifically the intent management system, may be configured convert or translate one or more external intents received from the external devices or systems into intents applicable within the intent-based application management system. For example, the intent management system may be configured to translate an application specified within the remotely received intent to one hosted on the one or more application servers, or may be configured to convert a resource identifier from a file type associated with an operating system of the remote device or system to a file type associated with the intent-based application management system.

The intent-based application management system may include a client device interface module configured to receive an input from one or more client devices of the plurality of devices. The client device interface module may be, for example, software running in the intent-based application management system which is configured to receive signals from one or more client devices e.g. via a network. The signals may originate due to, for example, a user hovering a cursor over or alternative clicking (e.g. right clicking) a graphical element displayed on their device which causes the client device to generate and transmit the signal. By interacting with the graphical element a context menu may be displayed including one or more intents provided by the intent-based application management system. Further navigating the context menu may provide a list of one or more applications which may execute operations associated with the intent.

In order to generate the intent based on the client device input, the intent-based application management system may further include an intent generation module configured to generate the intent based on at least the client device input.

The intent generation module may be configured to generate the intent by populating one or more fields of the intent based on at least the client device input.

Some or all of the plurality of fields forming the intent may be filled automatically, without the need for the user to specify the input. This could be based on a number of factors, e.g. the user of (or user account using) the client device, the make/model/type of the client device, the availability of native apps on the client device. The intent generation module may be configured to generate a requirement specification based on the factors including, e.g., various properties of the client device and/or the user of (or user account using) the client device from which the input is received. This requirement specification may then be translated into e.g. code which is used to populate the various fields of an intent. Various aspects of this process may be automated, in order to avoid the user having to input much information, or information which is based directly on the properties of the device or user.

The intent generation module may be configured to generate the intent further based on a detected property of the client device from which the input is received or the user of the client device from which the input is received. Applications and/or modules of the intent-based application management system may register events in an event register of the intent-based application management system. Considering, for example, system events, new intents could be generated or sent to the user as the events can be mapped to specific intents. For example, considering a device reagent consumption, a new intent for requesting that the reagent be refilled in a device could be sent to the user based on a mapping of events and intents.

The property (which may be a detected property) of the client device may include one or more of: a make of the client device, a model of the client device, a type of client device (e.g. whether the device is a smartphone, a tablet, a desktop computer, a laptop computer, or a bespoke piece of laboratory or point-of-care equipment configured to access the intent-based application management system), a geographical location of the client device (e.g. as detected by GPS), a status of the client device (e.g. as detected by a sensor, such as battery power, battery usage, these may form examples of events as discussed previously), a configuration of the client device. In order to achieve this, the intent generation module may include a property detection module configured to perform the detection.

The property (which may be a detected property) of the user of the client device may include one or more of: a persona or role of the user. Specifically, the intent-based application management system may specify a plurality of different personas or roles, each representing potential or likely users of the intent-based application management system. For example, the personas or roles may include: doctors, nurses, patients, hospital administrative staff, researchers, laboratory technicians, and the like. Persona may also define membership of a specific organisation, e.g. a hospital. Because people in each role are likely to have different requirements, provided by different apps, generating an intent based on persona or role ensures that they are provided with an improved user experience. Persona or role may also be detected by the property detection module. In some implementations, the property detection module may be configured to perform the detection of the property of the client device or the user thereof automatically. This automatic detection can be based on trained machine learning models (based on captured data from users and trained to detect patterns and so suggest next intents to the user automatically). The user may configure the intent-based application management system to automatically perform some of the intents suggested by the intent-based application management system on their behalf as soon as it complies with their workflows or relevant regulations.

In order to better explain the functions of the intent generation module, more information of the kinds of fields which a specific intent may include are provided. Two fields: the OPERATION field defining the kind of operation to be executed, and the DATA field, defining the data upon which (or in respect of which) the operation is to be executed have already been specified.

The fields in the intent may further include a CATEGORY field, which defines the manner in which the intent is executed.

Examples of categories may depend on the type of operation. For example, in the case that the operation is an OPEN operation, the CATEGORY field may specify that the determined application is launched in a new window or new tab on a display of the client device, launched from a launcher context, or launched in the same tab or same window. Alternatively, if the operation is a GET_CONTENT operation, or any other operation, the execution of which involves the retrieval of one or more data items, the CATEGORY field may specify the format in which the one or more data items are retrieved (e.g. in HTML format). The intent generation module may be configured automatically to populate the CATEGORY field based on e.g. the client device input or the detected property of the client device or the user thereof. For example, the intent generation module may specify that the retrieved content be displayed in a particular document format depending on whether the client device is a smart phone or a desktop computer, for ease of reading of the user.

The fields in the intent may further include a DATA TYPE field, which defines the type of data on which the operation is to be executed. The combination of the DATA TYPE and OPERATION fields may define the intent type. For example, the intent type may specify retrieval of patient data (i.e. the OPERATION is retrieval of data, and the DATA TYPE is patient data).

The fields in the intent may further include a COMPONENT field, which defines an application or a class of application which is to be used to execute the operation on the one or more data items.

Generally, an intent does not specify which application is to execute a given operation on the one or more data items. However, in some cases, the intent may include the COMPONENT field. In cases in which the intent is not to specify the application, the component field may be left empty.

The intent generation module may be configured to determine which applications are installed on the client device itself (i.e. native applications), and automatically to populate the COMPONENT field with those applications, or a subset thereof.

Alternatively or additionally, the intent generation module may be configured automatically to populate the COMPONENT field based on a determined property of the client device or the user thereof, as discussed earlier.

Specific types of operations which may be executed by applications of the plurality of application are now discussed. More detailed examples, and additional optional features are discussed in the "detailed description" section of this application too. It is important to differentiate between the type of operation and a specific operation. Herein, a "type of operation" is a high-level description of a generic operation such as opening an application, retrieving and displaying a record, and sending a message to a recipient. A "specific operation" refers to a specific instance of an operation, e.g. opening a specific application, retrieving and displaying a specific record, or a sending a specific message to a specific recipient. Execution of an operation may be divided into two broad categories:

1. Execution of the operation comprises opening one or more of the determined applications. It should be understood that the step of "opening an application" is an operation which is executed by the application.
2. Execution of the operation comprises performing some task by or within an application.

The operation to be executed may comprise opening an application, or retrieving one or more data items. When the disclosure is implemented in an HTML browser, the operation to be executed may be a GET operation. The operation to be executed may be triggered through a POST operation.

In some cases, the operation to be executed may comprise one or more of an OPEN operation, a GET operation, or a POST operation.

The one or more applications are determined by the application determination unit, using the intent registry. The intent registry is database containing information about which applications of the plurality of operations support which types of intent, or which on which types of data, or specific data. The intent registry may include a plurality of intent type nodes, each representing an intent type, and a plurality of application nodes, each representing an application of the plurality of applications. In addition, the intent registry may include a plurality of interconnecting edges, each of the edges connecting an application node with an intent type node, the intent type node corresponding to an intent type which is supported by the application to which the application node corresponds. From this underlying data structure, it may be possible to generate a lookup table, with the rows of a first column listing all of the supported intent types, and the corresponding rows of a second column identifying the one or more applications of the plurality of applications which are able to execute an operation associated with the intent type. It will be understood that in some cases, a plurality of applications will be able to execute the operation associated with a given intent type—i.e. a user of a client device may be offered a choice.

The intent management system may include an application registration module. Specifically, when a new application is loaded onto an application server, the application registration module may be configured to receive a registration request from the new application, the registration request including at least an application identifier (which may simply be the name of the application), and one or more intent type identifiers, each indicating an intent type supported by the application. Specifically, a supported intent type is an intent type for which the application is able to execute the associated operation. In response to receiving the registration request, the application registration module may then be configured to add one or more application nodes and/or intent type nodes to the intent registry.

Within the digital environment provided by the intent-based application management system, each individual user, or class of users, may be able to access different applications. For example, different users may be able to subscribe to different applications, which they may then access via the digital portal provided by the present disclosure. The digital portal may be accessed, for example, via a web browser on a device, or via an application installed on the device (e.g. an app on a smartphone). The intent-based application management system may include a user management database, stored, for example, at a user management module. The user management database may store associations between information identifying each of a plurality of registered users (e.g. in the form of a unique username, user ID or email address) and various other pieces of information, such as their role/persona (defined later in this application), as well as other personal details including contact information. Either the user management database, or a separate user security information database may store associations between information identifying each of the plurality of registered users and security information (such as a password, PIN, biometric data, secret questions and answers) which may be required for a user to access the intent-based application management system. The intent-based application management system may further include a session generation module (which may be referred to a session management module). When a user requests to access the intent-based application management system, the session generation module may be configured to receive a session generation request from the client device, and accordingly may be configured to generate a corresponding request for the user to enter their user information (the session generation module may be configured to do so by causing the GUI generation module to generate a dialogue box, or the like—discussed in more detail later in the application). Specifically, the session generation module may be configured to generate a request for information identifying the user of the client device, and corresponding security information. The session generation module, or a validation sub-module thereof, may be configured to validate the user input, e.g. by performing a lookup in the user management database, or the user security information database. If the user input is validated, the session generation module may be configured to generate a user session within the digital environment provided by the intent-based application management system. Herein, the term "user session" refers to a period of time during which that user is logged into the intent-based application management system, and has access (e.g. via a GUI) to the set of applications to which that user is either able to access by default, or because they have subscribed to them.

It has been discussed that the plurality of applications is located on an application server, and that in cases where an application is located on a client device, the client device may be considered to represent an application server. The intent-based application management system may include a plurality of application servers, each hosting at least one application of the plurality of applications. In implementations of the intent-based application management system in which there are a plurality of application servers, it should be understood that the intent registry stores information relating to all of the plurality of applications, regardless of which application server they are located on.

The plurality of application servers may include one or more of the following (this is not an exhaustive list):
Global application servers, which are accessible by client devices all over the world.
Regional application servers, which are accessible by client devices within a specified (e.g. geographic) region.
Local application servers, which are accessible by e.g. client devices connected to a specific local network or networks (i.e. the network or networks on which that local application server is located).

The apps on each of these types of application server are understood already to be accessible by the client device. However, in some cases, the appropriate application which is required (or desirable) to execute an operation associate with a given intent or intent type may not be accessible by the client device. In order to ensure that a user of the client device (or the client device itself) is still able to access the appropriate application, an application repository or marketplace server may be accessible by the intent-based application management system. Specifically, the one or more application server may include a marketplace application server, the marketplace application server hosting a plurality of applications which are not accessible by a client device. For example, the marketplace application server may take the form of a repository or source of applications which are not yet installed on a given client device. The intent registry may also include information relating to the plurality of applications which are hosted by the marketplace application server, specifically including intent type identifiers corresponding to operations that may be executed by the respective applications hosted by the marketplace application server. Registration of applications hosted by the marketplace application server may take place in the same manner as registration of an application on the other application servers (i.e. using the registration module). The intent registry may include information on which applications are located on which application server. For example, the lookup table may further include a column indicating the application server (e.g. using an application server ID) on which a given application is hosted. The intent registry may further include information specifying to which applications a given client device has access, for example in the form of a table storing information indicating whether an application associated with a given application identifier is or an application server associated with a given application server ID is accessible to a given client device.

The process which may be performed by the application determination module is now discussed. It may receive an intent from the client interface module, from the client device, or from the intent generation module. The application determination module may then be configured to perform a lookup in the intent registry in order to determine the one or more applications which are configured to execute the operation associated with the received intent. The application determination module may be configured to extract the intent type from the received intent, and to perform the lookup based on the intent type. Where the received intent includes an OPERATION field, the lookup may be based on the contents of the OPERATION field. Where the received intent includes an OPERATION field and a DATA TYPE field, the lookup may be based on the contents of the OPERATION field and the DATA TYPE field. Alternatively, the intent type identifier may include, or be derived from the data from the OPERATION field and the DATA TYPE field, and the lookup may be based on the intent type identifier. The application determination module may be configured to perform the lookup in a lookup table, as described previously in this application.

Based on the results of the lookup, the application determination unit may be configured to output application identifiers corresponding to one or more applications which are compatible with the intent type.

The applicant determination module may identify applications to which the client device has access. Accordingly, the application determination module may be configured to identify an accessible subset of the plurality of applications to which the client device has access. Then, the application determination module may be configured to identify only those applications in the accessible subset which are able to execute an operation associated with the received intent.

Then, in the event that the application determination module is unable to identify a suitable application in the accessible subset of applications, it may be configured to perform a lookup of the remaining applications in the intent registry. The applications which are present in the intent registry but which are not currently accessible by the client device may be hosted by a marketplace application server. In that case, the application determination unit output one or more applications hosted by the marketplace application server, and may give the user of the client device an opportunity to download or otherwise access those applications. This will be discussed in more detail later when referring to the user interface of the intent-based application management system.

Alternatively, the application determination module may be configured to search the whole intent registry, thereby outputting a list of one or more suitable applications. The application determination module may then be configured to determine, for each application, whether the client device in question has access to that application (e.g. because it is located on the client device, or because it is hosted by an application server to which the client device has access).

A user interface of the intent-based application management system is now considered. The present disclosure results in an overall improved user experience, by providing a centralized, and efficiently operating portal. A central feature of such a intent-based application management system is its user interface, and the manner in which it interacts with the various other components of the intent-based application management system.

The intent-based application management system therefore may include a graphical user interface (herein, "GUI") generation module, which is configured to generate GUI rendering instructions which, when received by the client device, cause the client device to render a GUI. The client device may then be configured to display the GUI on a display component. Such a GUI has two primary functions: to facilitate and receive inputs from a user, and to facilitate and display outputs to a user. These are discussed in turn below.

The GUI may include an input receiving object configured to receive the user input. The input receiving input may be in the form of a text input, a voice input, a gestural input or a clickable object.

When the input is e.g. a text input or voice input, the intent generation module may include a language processing module configured to generate the intent based on a received intent including natural language. Specifically, the natural language processing module may be configured to identify words in the input; the intent generation module may include an intent registry searching module configured to search the intent registry for the identified words, to identify one or more intent types related to the identified words; and the intent generation module may be further configured to generate an intent having one of the identified intent types. In some scenarios, there may be several intent types corresponding to the input. When the intent registry searching module identifies a plurality of intent types related to the identified words, the GUI generation module may be configured to generate instructions which, when received by the client device are configured to cause it to render a supplementary input receiving object, the supplementary input receiving object including a plurality of selectable options, each corresponding a respective intent type of the plurality of identified intent types; and the client interface module may then be configured to receive a selection input from the client device, the selection input indicating one of the plurality of identified intent types.

An important feature of the disclosure is its ability to provide a user with an integrated view of a plurality of different applications in a single display. There are two possible scenarios: the GUI may be configured to display an embedded snapshot of one of the applications, or alternatively, the GUI may be configured to display or render content such as data or information from the one or more applications in the GUI itself, without providing a snapshot of the application itself. Alternatively put, the GUI may include one or more embedded snapshots of in-application environments, and/or one or more application content display regions in which content (such as data or other information) from an application is displayed on the GUI, but not within a snapshot of the in-application environment. These snapshots or application content display regions may include input receiving objects, into which a user can make an input directly to the application, e.g. by typing into a text input, or by clicking a link. The intent generation module may then be configured to generate an intent based on the input, for example using the natural language processing module as discussed in the preceding paragraphs.

In order to provide the embedded screenshots or application content display regions, a given application may be configured to generate instructions, which when received by the client device, are configured to cause it to render an embedded snapshot of a predetermined in-application view in the GUI. Alternatively, the application may be configured to export application data to the GUI generation module which is then configured to generate GUI rendering instructions based on the exported application data.

The plurality of applications may include a subset of default applications or homepage applications which are automatically displayed in the GUI when the intent-based application management system of the present disclosure is accessed by a client device or a user of the client device. The default applications or homepage applications may be selectable by a user. Alternatively, the default applications or homepage applications may depend on the persona or role of the user of the client device, as discussed earlier with reference to the generation of an intent.

The process by which a user input is received, and then the operation associated with that intent is executed, is now discussed focusing on the latter feature.

A special case is considered first, in which the desired operation is the opening of one of the plurality of applications. In this case, an input receiving object on the GUI is configured to receive an input from a user of the client device, which may then be received via the client interface module. In some cases, the input may e.g. involve typing the name of the application to be opened, or clicking (or otherwise selecting) an image or other component associated with the application in question. It should be noted that the input receiving object in question could be displayed in either an embedded snapshot or application content display region. The use of intents, rather than specific application-based instructions, enables an input received in one application to result in the opening of, or use of, another application. The use of intents therefore enables interactions or interfacing between different applications, as well as between e.g. the applications and the intent-based application management system.

Optionally, in response to the selection or identification of the application in question, the GUI generation module may be configured to generate additional instructions which cause the client device to render a supplementary intent receiving object comprising a list of ways in which the application may be opened, for example opening the application in a new window, opening the application in a new tab, displaying an embedded snapshot of the application in the GUI homepage, or displaying content from the application in an application content display region of the GUI. The client device interface module may then be configured to receive a supplementary input from the user of the client device, e.g. as a result of them clicking one of the ways of opening the application in the list in the supplementary input receiving object.

Selection of an item in the list, or typing the name of the application does not itself represent an intent. Rather, in response to the selection of an application as outlined above, the intent generation module may be configured to generate an intent. In the case of opening an application, an OPERATION field of the intent may specify that the operation is to open an application, or to open the specific application. If the OPERATION field does not specify which application is to be opened, the DATA field may do so. Optionally, if the manner in which the application is to be opened is specified, then a CATEGORY field of the intent may define this.

At this point, the generated intent is sent to the intent management system. There, the application determination unit is configured to receive the intent, and to determine one or more applications configured to execute the operation associated with the intent. In this case, the operation is the opening of an application. Using the methods discussed earlier in this application, the application determination unit identifies the application. The intent management system may further include an application run module which is configured to cause the identified application to open, e.g. by sending an electronic instruction to the application server on which the application is hosted. At that point, the application opens. It should be noted that the application may be run on the client device, or it may run on an application server which is separate from the client device, and may be accessed by the client device via the GUI as discussed previously.

In other cases, the operation to be executed may be a specific operation on a specific data item, rather than broadly opening an application. In this case, the method is similar. An input may be received in the same way as for the previous case, though the steps performed after one or more applications have been identified may differ. In the case where only one application is available for the task (e.g. because only one application is able to execute the desired operation, or because the intent specified the COMPONENT, or other requirements of the application) the application run module may be configured automatically to cause the application to open and to execute the operation. Alternatively, particularly but not exclusively in the case that the application determination unit identifies a plurality of applications, the GUI generating module may be configured to cause the client device to render a supplementary input receiving object including a list of all the determined applications, in order to allow a user to select an application with which to execute the operation. The GUI generating module may be configured to cause the client device to render a preview of the one or more applications, e.g. to be displayed when the user of the client device locates a cursor over one of the applications in the list. The preview may be a "live" preview of the app, or may be a predetermined video or image file which is displayed. There are two scenarios which may arise here: the application may already be running on the intent-based application management system, or it may have to be opened first.

In the first case, the application is already running. For example, the intent-based application management system may implement "software as a service" (SAAS) in which users of the client device are able to access application servers provided by an application provider. In these cases, all of the applications on the servers may be running constantly in the background, and when a user selects the application from e.g. the list displayed in the supplementary input receiving object, a [XXX] causes the GUI generation unit to send instructions to the client device which cause it to display either an embedded snapshot or an application content display region on the GUI. Alternatively, a [XXX] module may cause the application to open in a new window, or a new tab on the client device. This applies primarily to cases in which the application is not hosted by the client device. In some cases, an embedded snapshot of the application or an application content display region may already exist in the GUI, in which case the GUI does not perform this step. Once the application is viewable or accessible by the user of the client device, the operation associated with the intent is executed.

If the application is not already running, then the steps outlined above with reference to opening of the application take place. Then, the application may execute the operation associated with the intent.

When a plurality of applications is suitable for a particular operation, or meet the requirements of the intent, the application determination unit, or a prioritization module thereof, may be configured to rank the list of applications. The prioritization module may be configured to rank the suitable applications based on one or more of the following factors: a persona or role of the user (as defined previously), a user's usage history (e.g. those applications which the user has used frequently in the past may be ranked higher than those applications which the user has never used), a collective usage history of all users having the same or similar persona or role as the user (this effectively combines the previous two factors) and/or the application servers hosting the applications (e.g. applications which are hosted on the client device may be ranked higher than applications which are hosted on distant servers. Applications which are hosted on the marketplace server may rank even lower).

How the execution of the operation actually takes place is now considered in more detail, after the application to be used has been identified and/or selected by a user. In some implementations, the intent-based application management system may include an instruction generation module configured to generate instructions corresponding to the intent, the instructions configured to cause the application to execute the operation associated with the intent. In order to simplify the nature of the instructions, thereby reducing the burden on the intent-based application management system, each application of the plurality of application is configured to expose an API to the intent-based application management system. Specifically, the instruction generation module of the intent-based application management system may be configured, based on the intent, to input instructions into the exposed API, the instructions configured to cause the application to execute the operation associated with the intent.

Security is an important aspect of any distributed computer-based system. With the present disclosure, there are two main security aspects: permissions management, and consent management. Broadly speaking, permissions management concerns access control rules relating to whether a broad class of user or persona is permitted to execute various operations, e.g. based on their persona or role, or their location. Consent management relates to whether or not a specific person has consented to another person or organization accessing data about that person.

Permissions management and consent management are discussed below. At a high level, however, the intent-based application management system may include an access control module configured to determine whether a client device or user of the client device (these are referred to collectively as an "entity" herein) is permitted to execute the operation which is associated with an intent received from that entity. Determination of permission may be executed in two stages: firstly, it may be determined whether the entity is permitted to execute the operation based on e.g. the persona and geographic location of the entity. Then, for certain specific operations, the execution of which requires explicit consent from another party (e.g. a person such as a patient, or an organization as a whole), it may be determined whether the entity has the required consent to execute the operation. In this application, the former determination is referred to "permissions management", and may be performed, effected, or facilitated by a permissions module, and the latter determination is referred to as "consent management" and may be performed, effected, or facilitated by a "consent management module". These modules are discussed below. It should be noted that the permissions management and the consent management may be performed in either order, and may be performed simultaneously, or in parallel. The permissions module and the consent management module may both be comprised by the access control module. It should be noted that the present disclosure differs from known permissions and consent management systems and processes in that the determination is made at the level of a specific intent which is associated with the operation to be executed.

Where the permission or consent is dependent on the identity of a user of the client device (i.e. rather than the client device itself), the permissions module or consent management module may be configured to determine who the user of the client device is, for example by identifying which user is currently logged in on the client device. The permissions module or consent management module may request this information from the session generation module. The permissions module or consent management module may be configured to determine characteristics (e.g. the role or persona) of the user by performing a lookup in the user management database.

The intent management system may include permissions data. Specifically, the intent management system may include a permissions table containing the permissions data. Alternatively, the intent registry may contain the permissions data. The permissions data may define those operations which a given entity or class of entity is permitted to perform. In other words, the permissions data may associate characteristics of the entity or class of entity, with aspects of the operation which is associated with the received intent. For example, the permissions data may define, for each of a plurality of entities or classes of entities, one or more of the following:

one or more intent types, the operations associated with which the entity or class of entities is permitted to execute.

one or more operations types which the entity or class of entity is permitted to execute.

one or more data types on which the entity or class of entity is permitted to execute operations.

one or more specific data items on which the entity or class of entity is permitted to execute operations.

It should be noted that the permissions data may simply stored associations between the entities or classes thereof and the permitted operations/intent types/data types/data items—this does not necessarily mean that the permissions data is sorted by entity or class of entity. However, in some cases, the permissions data may include a lookup table, including in a primary column (or row) a list of entities and/or classes of entities, and in a respective plurality of secondary columns information identifying the permitted intent types, operation types, data types and/or specific data items. Alternatively, the permissions data may include a plurality of lookup tables, each directed towards only one of the specific permitted features.

Alternatively, rather than being arranged by entity or class of entity, the permissions data may additionally or alternatively include a lookup table having in a primary column any one of the intent type/operation type/data type/specific data items, and in a secondary column, information identifying the entities or class of entities who are permitted to execute an operation associated with the intent type/execute an operation/execute an operation on that data type/execute an operation on the specific data items. In implementations in which the lookup table is arranged by intent type, the secondary column may be incorporated into the intent registry.

As discussed, an entity may be a client device, or a user of a client device. Herein, a class of entity may represent a person or role of a user. A class of entity may also represent the set of entities which are located within a given geographical area.

The operation of the permissions module is now considered. Specifically, the intent management system or an access control module thereof may include such a module. At a high level, the permissions module is configured to determine whether a specific entity (which may belong to a class of entities) is permitted to execute a specific operation associated with an intent received from that entity. This determination may be based on permissions data as defined in the preceding paragraphs. Herein, the term "specific operation" refers to the exact operation to be performed, e.g. the operation itself, the manner in which it is operated, and the data on which it is to be executed. This is in contrast to the "intent type" or "operation type", which does not, for example, specify the data on which the operation is to be executed.

In order to determine whether the client device is permitted to execute the specific operation associated with the received intent, the permissions module may be configured to determine, based on the permissions data, whether the entity (or class to which that entity belongs) is permitted to do one or more of the following:
  execute an operation (i.e. any kind of operation) associated with the intent type of the received intent.
  execute the type of operation specified in the received intent.
  execute an operation on the data type specified in the received intent.
  execute an operation on the specific data items specified in the received intent.

In the case where the permissions are set at the level of classes of entities, rather than the entity itself, the permissions module may first be configured to determine to which class the entity belongs.

The permissions management steps described above may take place before the application determination module determines the suitable one or more applications. In other words, the permission module may be configured to determine the permissions as outlined above before the intent is received by the application determination module. Alternatively, the steps may take place in parallel, i.e. simultaneously.

In some cases, there may be an alternative or additional permissions management step, which takes place after the application determination module has determined the one or more suitable applications. Here, a decision may be made based on whether an entity or class of entity is permitted to access the applications in question. Specifically, the permissions module may be configured to determine whether an entity or class of entity is permitted to use or access one or more applications. In other words, after the application determination module has determined the one or more applications, the permissions module may be configured to determine, for each of the one or more determined applications, whether the specific entity is permitted to use or access that application. The permissions module and/or the application determination module may then be configured to identify a permitted subset of the determined applications. In order to achieve this, the permissions data may further define specific applications of the plurality of applications (and optionally, applications hosted on application servers to which the entity does not yet have access to) which an entity or class of entity is permitted to access or use. Alternatively, and equivalently, the permissions data may define, for each of the plurality of applications, the entities or classes of entities which are permitted to access or use that application. As before, the permissions data could be encoded in a lookup table.

Above, the manner in which the permissions module is configured to determine whether an entity is permitted to execute a specific operation associated with the received intent was explained. What happens after this determination is made is now considered. There are three possible scenarios:
  i. the entity is fully permitted to execute the specific operation associated with the received intent.
  ii. the entity is partially permitted to execute the specific operation associated with the received intent.
  iii. the entity is not permitted to execute the specific operation associated with the received intent.

These cases are discussed in turn.

CASE (I): In some cases, the permissions management may take place before the intent is passed to the application determination module. In those cases, after the positive determination has taken place, the intent management module or the permissions module may be configured to transmit, send, or direct the received intent to or towards the application determination module for subsequent processing. Alternatively, if the permissions management takes place after the determination of one or more suitable application, then after the positive determination, the steps which have been described previously in the application after the determination has been made can then take place, e.g. displaying the one or more applications to the user via the GUI.

CASE (II): There are two possible outcomes if the entity is only partially permitted to execute the specific action associated with the received intent. Firstly, after the determination has been made, the process may end, and the received intent may then not be passed on to the application determination module, or the list of suitable applications may not be presented to the user via the GUI. Alternatively, steps may be taken to ensure that the specific operation associated with the intent is only partially executed. Consider a case where the received intent may be divided into two distinct parts, for example if it defines an operation to be executed on a first data item and a second data item, or a first data type and a second data type. Alternatively, the received intent may specify two operations to be executed on a data item or items. When an intent may be divided in this way, reference is made to a first specific sub-operation and a second specific sub-operation. It will be appreciated that the specific sub-operations need not be restricted to operation type, data type, or specific data items. In that case, the permissions data may define that the entity from whom the intent was received is permitted to execute the first specific sub-operation, and is not permitted to execute the second specific sub-operation. In that case, if the determination is performed before the intent is received by the application determination module the application determination module may be configured only to determine one or more applications configured to execute the first specific sub-operation which is associated with the received intent. Alternatively, the permissions module (or any other module) may be configured either to modify the intent to remove the data relating to the second specific sub-operation, and only send this modified intent to the application determination module. Alternatively still, the permissions module or intent generation module may be configured to generate a new intent based on the determination by the permissions module, the new intent including only data relating to the first specific sub-operation, and to send this newly-generated intent to the application determination module.

If the determination is performed after the application determination unit has determined one or more applications configured to execute the specific operation associated with the intent (including the first specific sub-operation and the second specific sub-operation), the intent-based application management system may prevent the user from executing the second specific sub-operation, for example by displaying an error message, or simply by executing only the first specific sub-operation. In such cases, the GUI generation module may be configured, in response, to generate instructions which cause the client device to display an error message informing the user thereof why the operation associated with the received intent has not been executed in full.

CASE (III) When it is determined that the entity is not permitted to execute the specific operation associated with the received intent, the process may simply stop. For example, after the negative determination has been made, the permissions module may be configured to prevent the intent from being sent to the application determination module. If the negative determination takes place after the application determination module has determined the one or more applications, the intent-based application management system may prevent the user from executing the operation. In such cases, the GUI generation module may be configured, in response, to generate instructions which cause the client device to display an error message informing the user thereof why the operation associated with the received intent has not been executed.

Permissions may be validated at two levels: the domain level, and local level. In the present context, by "domain level" reference is made to access to specific resources (e.g. the ability to access devices, patient results and/or demographics, or to manipulate values related to quality control). In contrast, local level takes into account the location and the persona of the user. For example a user may be able to access all data for a hospital in a specific area, but only when it is determined that the user is within a predetermined geographical area.

The permissions module may be configured to make the determination or determinations (i.e. regarding access permission) in response to receiving the intent from the client device.

Rather than having a devoted permissions module, the application determination module may be configured to perform the determination as outlined in the above steps. How the outcome of the various determinations is manifest is discussed after discussion regarding consent management, since the result seen by the user is the same.

Now that permissions management has been discussed, consent management is considered.

Consent management applies to cases where an intent relates to an operation which, when executed, will give a client device (or a user thereof) access to data items which include personal data. In many places, it is illegal to access personal data pertaining to a given individual without the express consent of that individual. Below a manner in which a consent management scheme may be technically implemented in the intent-based application management system of the present disclosure is set out.

Consent management is relevant for documents, records, and other data which relates to an individual or group of people, herein referred to as the "subject". For this reason, consent may be managed at the level of data items, or groups of data items. In one example, each data item or group of data items may have associated consent metadata which defines those entities or classes of entities which are permitted to access the data items. Here, "access" means to execute an operation on or in respect of the data item(s), for example to view it, to retrieve it, to make a copy of it, or to edit it. The consent metadata may be generated at the point when the data item or group of data items themselves are generated. For example, if the data items pertain to a patient's medical history, the consent metadata may be generated at a medical appointment. The content metadata may include a set of fields, each field associated with a given entity or class of entity (defined as previously). The content metadata may define, for each field, whether that entity or class of entity is permitted to access the data item. Alternatively, the content data may include only information concerning the entities or class of entities which are permitted to access the data item. In the case of a medical record, the person or patient may have the opportunity to specify these entities or classes of entities at e.g. a medical appointment, or when first registering to a surgical practice. A given set of data items may include a first subset of data items having first consent metadata and a second subset of data items having second consent metadata.

Additionally, or alternatively, the consent management module may include consent management data. This is analogous to the permissions data described earlier. The consent management data may, for each of a plurality of data items, define those entities or classes of entities which are permitted to access that data. Alternatively, the consent management data may, for each of a plurality of subjects, define entities or classes of entities which are permitted to access data items relating to those subjects. As before, these may be implemented in the form of lookup tables. In some cases, the consent management module may be configured to generate the consent management data based on a consolidation of the consent metadata from a plurality of data items.

In addition, the consent management data and the permissions data may be collated together into a single database.

The operation of a consent management module is now considered, which is analogous to the operation of the permissions module, with a narrower remit. The intent management system or an access control module thereof may include the consent management module. The consent management module, like the permissions module, is configured to determine whether a specific entity is permitted to execute an operation on a data item or data items, the operation associated with an intent received from that entity, the determination based on consent management data or consent metadata specified by the subject of the data item or data items. Where the consent management data or consent metadata is defined at the level of classes of entities, rather than individual entities, the consent management module may be configured to determine to which class the entity belongs.

As with the permissions module, there are three possible outcomes from the consent management module:
the entity is fully permitted to execute the operation on the data items specified in the received intent.
the entity is partially permitted to execute the operation on the data items specified in the received intent.
the entity is not permitted to execute the operation on the data items specified in the received intent.
These cases are discussed in turn.

CASE (I): In some cases, the consent management may take place before the intent is passed to the application determination module. In those cases, after the positive determination has taken place, the intent management module or the consent management module may be configured to transmit, send, or direct the received intent to or towards the application determination module for subsequent processing. Alternatively, if the consent management takes place after the determination of one or more suitable application, then after the positive determination, the steps which have been described previously in the application after the determination has been made can then take place, e.g. displaying the one or more applications to the user via the GUI.

CASE (II): There are two possible outcomes if the entity is only partially permitted to execute the operation on the data items specified in the intent. Firstly, after the determination has been made, the process may end, and the received intent may then not be passed on to the application determination module, or the list of suitable applications may not be presented to the user via the GUI. Alternatively, steps may be taken to ensure that the specific operation associated with the intent is only partially executed. Consider a case where the received intent may be divided into two distinct parts, for example if it defines an operation to be executed on a first data item and a second data item. In that case, the consent management data may define that the entity from whom the intent was received is permitted to execute an operation on the first data item, but is not permitted to execute an operation on the second data item. In that case, the consent management module (or any other module) may be configured either to modify the intent to remove the second data item from e.g. the DATA field, and send this modified intent to the application determination module. Alternatively still, the consent management module or intent generation module may be configured to generate a new intent based on the determination by the consent management module, the new intent specifying only the first data item in the DATA field to send this newly-generated intent to the application determination module.

If the determination is performed after the application determination unit has determined one or more applications configured to execute the specific operation associated with the intent (specifying both the first data item and the second data item), the intent-based application management system may prevent the user from executing the operation on the second data, for example by displaying an error message, or simply by executing the operation only on the first data item. In such cases, the GUI generation module may be configured, in response, to generate instructions which cause the client device to display an error message informing the user thereof why the operation associated with the received intent has not been executed in full.

CASE (III) When it is determined that the entity is not permitted to execute the operation on the data items specified, the process may simply stop. For example, after the negative determination has been made, the consent management module may be configured to prevent the intent from being sent to the application determination module. If the negative determination takes place after the application determination module has determined the one or more applications, the intent-based application management system may prevent the user from executing the operation. In such cases, the GUI generation module may be configured, in response, to generate instructions which cause the client device to display an error message informing the user thereof why the operation associated with the received intent has not been executed.

The application determination module may be configured to receive an intent having the OPERATION type "retrieve data", or the like. The intent may have specified data pertaining to a particular individual, the data including a plurality of data items. The application determination module may be configured to identify an application which is able to retrieve the selected data, and open that application as described previously in this application. At some point before the data is opened and displayed, a consent management module of the intent-based application management system may be configured to determine whether the client device is permitted to access the requested data items. This determination is made based on the consent metadata associated with the requested data items, and based on the entity or class of entity requesting the data (which could be based on the geographic location, role or persona of the user). Consent management differs from permissions management in that it is defined by a person or user, and assessed at the level of individual data items.

Where intent-based application management systems according to the present disclosure are used for the handling of e.g. medical or other personal data, it is important to keep track of who has request access to which data, and whether or not that access was granted. Accordingly, the intent-based application management system may further include a data access tracking module which is configured to track the activity of entities using the intent-based application management system for successful and unsuccessful actions from users and systems. According to the present disclosure, the activity is tracked based on the intents which are received by the intent-based application management system.

Specifically, the data access tracking module is configured to generate tracking data, and to store it to a data tracking management database. When an intent is received at the intent-based application management system, e.g. at the client interface module, the data access tracking module may be configured to generate an entry in the data tracking management database, the entry including information identifying the entity from whom the intent was received, and the one or more data items on which the specific operation associated with the intent is to be executed. Where the entity includes a plurality of fields, the tracking data may include the data present in each of those fields. In order to identify these fields, the data access tracking module may include an intent data extraction module configured to extract the data from the fields of the intent. In addition to the content of the intent, which effective represents a request for an operation to be performed, the data access tracking module may also configured to determine whether the specific operation was permitted or consented to. Accordingly, the data access tracking module may be configured to receive input from the permissions module and/or the consent module, the input including an outcome of the determination performed by those modules. In cases where the specific operation is only partially permitted, the data access tracking module may be configured to generate a plurality of entries, each corresponding to a specific sub-operation, as defined earlier in this application, and to associate respective data (i.e. the data item, with each of these entries. In some embodiments, a data access tracking module, configured to track the activity of client devices or user accounts of client devices using an application management system, may track successful and unsuccessful healthcare data operations or actions.

If the tracking data is generated in the form of a set of associations between various data points, it is possible to render it in a number of forms. The tracking data may be rendered in the form of a table. In some cases, the tracking data in the table may be sorted based on the entity, in order to show all of the data items to which an entity has either accessed or requested to access. Here "access" should be understood to mean "execute an operation on". Alternatively, the tracking data may be sorted by data item, in order to show all of the entities who accessed or requested to access a particular data item.

The intent-based application management system may include a search module. This may be used by users of the intent-based application management system to perform a search on all data stored by the intent-based application management system to which a given user has access. The provision of a search module which enables a user to perform a global search of information in all applications (as well as some other sources) is advantageous as it provides a user with the ability to search all the applications from a single input, rather than having to perform individual searches within the various applications and other sources of data.

As discussed, the GUI may include an input receiving object. This may be configured to receive a search input. Alternatively, the GUI may include a specific search input receiving object which is configured to receive a search input. The search input may be received via the client device interface module.

In some cases, the (search) input receiving object will be configured to receive an "informal" search input, e.g. it may include a plurality of separate input fields, the text in each serving a different function within the search query, e.g. "results must include", "results must not include", and "results may include any one of". In that case, the intent-based application management system may include a query generation module configured to generate a formal search query based on the informal search input. However the search function of the intent-based application management system may be intent-based. Specifically, the intent generation module may be configured to generate a search intent based on the search input, or based on a query generated by the query generation module.

The OPERATION field of the search intent may be a SEARCH operation. The DATA field of the search intent may define the data which is to be searched. The data which may be searched may include one or more of the following:
  user information from the user management database.
  Information collected from the portal (including notifications and events, i.e. notifications that were raised historically and system events that may have happened in the ecosystem if they are published by the platform or specific applications).
  Data provided by the applications to which a given user has access.

The search module may be configured to generate search results, which are the data items which meet the requirements of the search input or the query. In order to generate the search results, the search module may be configured to search a search database, which is an internal database which is fed with data collected from all of the applications to which the user has access, as well as e.g. data from the user management database and the information collected from the portal. In this way, the search module need only search a single database. Alternatively, the search module may be configured to generate a respective search request for each source of data (i.e. the applications to which the user has access, the information collected from the portal, and the user management database), and to transmit the requests to the respective sources. The search module may then be configured to receive a respective plurality of responses from the sources of data, the responses including the data item or data items which meet the criteria specified in the search input or the search query. The search requests may be in the form of intents. The search results may be filtered based on the user's permissions and/or access rights.

Alternatively, the search module may be configured to send the search query or the searching intent to the intent management system, which is then configured to generate the search requests and to transmit them to the respective sources. The intent generation module of the intent management system may be configured to generate the individual search requests in the form of intents.

Not all of the applications may provide the search functionality. The intent registry or another application information database may include information defining whether each application of the plurality of applications provides the search functionality. In cases where the information is provided in the intent registry, the search module may be configured to generate a lookup table from the data in the intent registry which displays only the information regarding the applications and whether or not they provide the search functionality, rather than all of the (in this case) superfluous information such as supported intent types and permissions and consent management information.

The outputs of the search module, i.e. the search results, may include any or all of the following features:
  1. Each search result may specify the source of that search result. For example, the search result may specify whether it came from the user management database, the information collected by the portal, or from one of the applications. If the search result came from one of the applications, the search result may state which application.
  2. Each search result may specify a date associated with that search result.
  3. Each search result may include a quality score. The quality score quantifies how well the search result meets the search input, e.g. in terms of the number of co-occurring terms, or based on another similarity metric. The search module may include a prioritization module configured to rank the search results in order of their quality score.

4. Each search result may include a match number indicating how many of the words in the search result match the words in the search input.

5. Each search result may include one or more intents. Specifically, the search module or another component of the intent-based application management system may be configured to generate an intent corresponding to the search result. For example, the intent generation module may be configured to generate the intent, which is received by the search module along with the other components of the search result. The GUI generation module may be configured to generate an input receiving object which is associated with the intent such that a predetermined input causes the intent to be sent to the intent management system. The intent may then be received by the application determination module as normal. In some cases, the generated intent may specify the application (e.g. in a COMPONENT field) which is to be used to execute the operation associated with the intent. The input receiving object may be a clickable or otherwise selectable hyperlink.

The user performing the search may not have permission to access all of the results of the search, or the subject of a data item which would ordinarily have been returned as a search result may not have consented to that data item being viewed by e.g. that specific user, or the role/persona of the user. In order to ensure that a user is not given access to data items to which they are not permitted access, the permissions module and consent management modules may also play a role in the search process, in an analogous way to the process by which the intent-based application management system is used to determine an application based on a received intent. For reasons of conciseness, no repetition in detail the roles of the permissions module and the consent management module is made here. The permissions management or consent management steps (i.e. the determination whether an entity is permitted to perform a specific operation associated with an intent, or whether an entity is permitted to access a given data item or data items) may take place after the search results are determined, i.e. to provide a filter which ensures that only the permitted results are displayed to the user. Specifically, the permissions module and/or consent management module may determine whether a user has permission to execute the specific operation which is associated with the intent which forms part of a search result, as discussed above.

The searching module may be configured to sort the one or more search results before presenting them to the user. The sorting may be performed, for example, based on: a type of search result, a source of the search result, a history of a user of the client device, a history of an organisation of which the user of the client device is a member, a role of a user of the client device, a history of a user comparable to the user of the client device. The sorting may, for example, be implemented using a machine-learning based sorting algorithm trained on real or synthetic data.

When a certain event takes place, it may be desirable to generate and display a notification to the user of the intent-based application management system. As with all of the other features of the disclosure, this process can be improved through the use of intents. Accordingly, the intent-based application management system of the present disclosure may further comprise a notification module. An application of the plurality of applications may generate an event, or may detect an event (e.g. receiving an email, or sending a calendar reminder). It may be necessary to inform a user of the client device about the occurrence of the event. Accordingly, the notification module may be configured to receive a notification generation request from an application. The notification generation request may include information about the nature of the event about which the user of the client device is to be notified, such as the application, the time/date, and in some cases, the notification generation request may include an intent to be included in the notification. By including an intent in the notification itself, the user of the client device who receives the notification may execute, from the notification itself, an operation associated with the notification. The intent generation module may receive a request to generate the intent from the application, and the notification module may receive the intent from the intent generation module. In response to receiving the notification generation request, the notification module may be configured to generate a notification, the notification may include information about the nature of the event. This information may be the same as discussed previously. The notification module may then be configured to send the notification to the client device. The notification may contain instructions which, when received by the client device, causes it to display the notification. The notification may be displayed either only when the user is accessing the intent-based application management system of the present disclosure, or the notification may be displayed by the operating system of the client device even when the user is not accessing the intent-based application management system of the present disclosure. The notification module may be configured to sort notifications received before presentation to the user, and to present them to the user based on the results of the sort (e.g. by priority). The sorting may be performed, for example, based on: a type of notification, an intent associated with one or more of the notifications, a history of a user of the client device, a history of an organisation of which the user of the client device is a member, a role of a user of the client device, a history of a user comparable to the user of the client device. The sorting may, for example, be implemented using a machine-learning based sorting algorithm trained on real or synthetic data.

The notifications may be from any one of the following sources: a digital hub or portal, an edit operation (e.g. patient, order, sample, results, test, tube, device, practitioner, practitioner certificate), a patient related operation (e.g. discharge, admission, transfer), a device operation (e.g. update, calibrate, refill, monitor, start/warm up), an order/sample operation (e.g. review, update, create), a results related operation (e.g., review, comment, approve/validate), a practitioner related operation (e.g. invite, assign to team, assign to task, disable, discharge), a practitioner certificate operation (e.g. update, recertify, plan training), a request operation (e.g. more reagents/strips based on consumption and material/lot management information), a password update or change request operation, a review device connectivity status operation (e.g. based on events of "connected/disconnected"), a quality review operation (e.g. perform, report, comment, approve/validate), a global search operation (e.g. for applications which support searching through the portal), and a view content and raw data operation (e.g. view content or raw data in an HTML based view or JSON format).

In particular, the notification may include an intent. In cases where the intent is not received from the application as part of the notification generation request, the notification module may be configured to request that the intent generation module generates an intent, and transmits it to the notification module. Like with the search results, the notification may include an input receiving object (which may be generated by the GUI generating module) such that a predetermined input causes an intent to be sent to the intent management system. The intent may be then be received by the application determination module as normal. In some cases, the intent may specify the application (e.g. in a COMPONENT field) which is to be used to execute the operation associated with the intent. the input receiving object may be a clickable or otherwise selectable hyperlink. When the intent does not specify the application to be used, it is possible that the application which generated the notification in the first place is not the application which is used to execute the operation associated with the intent. The notification may include a plurality of intents.

In a first case, the intent-based application management system of the present disclosure may be used in an order management workflow. In this case, the plurality of applications may include an order management application. In this context, an "order management application" is an application which allows a user to select one or more desired products and/or services, and to request that those products and/or services be delivered to them, or to another address of their choice. A user may input their desired order in a number of ways. If the user of the client device knows which application they would like to use, they can manually open the application. Alternatively, an input receiving object of the GUI may be configured to receive an input from a user:

The input may identify the application which the user of the client device would like to use. In that case, the natural language processing module may be configured to identify the name of the application in the input, and to cause the intent registry searching module to search the intent registry for intent types including the identified application name. Then, the GUI may subsequently be configured to generate instructions, which when received by the client device, are configured to cause it to render a supplementary input receiving object, which includes one or more selectable options, each corresponding to a different intent type of the plurality of identified intent types. For example, the supplementary input receiving object may include a plurality of options, each option corresponding to an application which contains the name which is typed into the input receiving object initially. The client interface module may be configured to receive a selection input indicating the intent type which specifies that the order management application be opened. Then, the order management application may be opened in a new window or tab. Alternatively, an embedded snapshot of the order management application may be displayed within the GUI. Alternatively, the order management application may export application data to the GUI generation module, thereby configuring the GUI generation module to generate GUI rendering instructions based on the exported application data. The user may then user the order management application to generate an order for the desired product/service.

Rather than opening the order management application, the user may take advantage of the intent-based ecosystem provided by the present disclosure. Specifically, the intent-based application management system of the present disclosure provides an interface between the portal or the GUI and the order management application, meaning that a user is able to execute in-application operations without having to open the application and to navigate the in-application environment. Here are two examples of how an order may be generated in this way:

1. A user may input an instruction such as "order [product]" in an input receiving object. The intent generation module may then be configured to generate an intent based on this input, for example by using the natural language processing module, as outlined previously. Alternatively, if there are a number of intents which correspond to the input, a supplementary input receiving object may be generated as displayed, as before. The supplementary input receiving object will include at least one intent corresponding to the desired order. In some cases, there may be a plurality of order management applications, in which case the supplementary input receiving object may include options such as "order [product] from [application A]" and "order [product] from [application B]". In response to selection of one of the options, the instruction generation module may be configured to generate instructions corresponding to the selected intent. Alternatively, in response to the user input, if there are a plurality of intent types which correspond to the user input, the supplementary input receiving object may include a plurality of different intent type options. Then, in response to a selection of one of the intent types, a further supplementary input receiving object may be generated, which lists the possible applications including the order management application. After the selection of one of the applications, the process may continue as above.
2. The user may use the search function of the present disclosure to generate the intent. Specifically, the user may input the name of the product/service into the search input receiving object. The search process may take place as outlined earlier in the application. Then, a number of search results may be presented, each including a corresponding intent. Then, from this point, the same steps referred to in the latter half of point 1 above may be performed in order to execute the operation associated with the intent, i.e. ordering the product.

The intent-based application management system of the present disclosure may advantageously be used to implement task management, for example using a task management application. Herein, the term "task management" refers to the management of a series of actions that must be performed by a user or other entity. A task management application could be used to implement a workflow, for example, or could be used to control the operations performed by a piece of laboratory equipment. The process by which the task management application is opened, or accessed, is the same as above for the order management process. This is described in general terms before discussing how it may be applied to the order management example explained above.

In this context, a task is not the same as an intent.

The task management application may be configured to store, for a particular entity, information pertaining to one or more tasks to be completed by that entity. The entity may refer to a specific user, a group of users, a device, a group of devices, or the like. There are two key processes which may take place: editing a list of tasks (in particular, adding a task), and accessing the list of tasks (with a view to executing one). In the following example, users are referred to as setting a number of tasks to be performed by a piece of laboratory equipment, but it will be appreciated that this could also apply equally well to a scenario in which a list of tasks is collated for a (human) user or team. As mentioned, the task management application can be opened/accessed using the same process as was described above for the order management process. In order to add a new task, a user may make an input corresponding to an "add task" intent. In response, a supplementary input receiving object may be displayed, which allows the user to specify a device whose task the list the task should be added to. Alternatively, the user's input may specify both the device and the task. Then, the intent generation module 1109 may be configured to generate an intent corresponding to the user's desired input, and to submit the intent to the application via the intent management system (e.g. by specifying the task management application in the COMPONENT field of an intent). The operation which is associated with the intent is the addition of the specified task to the task list of the specified device. A corresponding process may take place with regard to editing an already existing task in the device's task list.

The laboratory equipment or, correspondingly, the user may then also submit an intent in a similar way in order to access its own task list. More specifically, an application which controls the operation of the laboratory equipment may submit the intent. In the case of the laboratory equipment, it may be configured automatically to carry out the tasks defined in its task list. When the task is complete, the equipment may be configured to submit an intent in order to automatically remove the task from the list. In this way, the intent-based application management system is able to exploit the use of intents for automatic control of laboratory equipment.

In a second aspect, the disclosure provides a system accessible by a plurality of client devices via a network, the system including:
  an application server hosting a plurality of applications;
  an intent management system including:
    an intent registry storing information about a plurality of intent types;
    an application determination unit configured to receive an intent, and to determine, using the intent registry, one or more applications associated with the received intent; and
  a processor configured to open one or more of the determined applications associated with the received intent.

The system may be an intent-based application management system, and may include any one, or any combination insofar as they are compatible, of the optional features set out with reference to the first aspect.

In a third aspect, the disclosure provides an intent management system accessible by a plurality of client devices via a network including:
  an intent registry storing information about a plurality of intent types, the information including, for each intent: an intent type identifier, and one or more applications configured to execute an operation associated with the intent type;
  an application determination unit configured to receive an intent, and to determine, using the intent registry, one or more applications configured to execute an operation associated with the received intent.

The intent management system of the third aspect may be the same as the intent management included in the intent-based application management system of the first aspect, and may include any one, or any combination insofar as they are compatible, of the optional features set out with reference to the first aspect.

In a fourth aspect, the disclosure provides a server or group of servers hosting the system of the first, second, or third aspects. The server or group of servers may be physical servers (e.g. running on dedicated hardware), virtual servers, or combinations thereof.

In a fifth aspect, the disclosure provides a computer-implemented method of managing intent-based applications and/or facilitating execution of an operation by an application, the method including the steps of:
  receiving an intent;
  determining, using an intent registry, one or more applications configured to execute an operation associated with the received intent, wherein:
    the intent registry stores information about a plurality of intent types, the information including, for each intent: an intent type identifier, and one or more applications configured to execute an operation associated with the intent type; and
  executing the operation associated with the received intent using one or more of the determined operations.

The method of the fifth aspect may have any one, or any combination insofar as they are compatible, of the optional features set out with reference to the first aspect.

In a sixth aspect, the disclosure provides a computer-implemented method of facilitating access to an application:
  receiving an intent;
  determining, using an intent registry, one or more applications associated with the received intent, wherein:
    the intent registry stores information about a plurality of intent types; and
  opening the application associated with the received intent.

The method of the sixth aspect may have any one, or any combination insofar as they are compatible, of the optional features set out with reference to the first aspect.

Further aspects of the present invention provide: a computer program comprising code which, when run on a computer, causes the computer to perform the method of the fifth and/or sixth aspect; a computer readable medium storing a computer program comprising code which, when run on a computer, causes the computer to perform the method of the fifth and/or sixth aspect; and a computer system programmed to perform the method of the fifth and/or sixth aspect.

BRIEF DESCRIPTION OF THE DRAWINGS

FIGS. 3A and 3B are examples of tables which may be included in the intent registry;

FIGS. 6A-6E show examples of permissions tables containing permissions data used in the permission management process;

FIG. 9A shows an example of a searching process, and FIGS. 9B and 9C illustrate different ways in which the research results may be generated;

DETAILED DESCRIPTION

Figure 1:
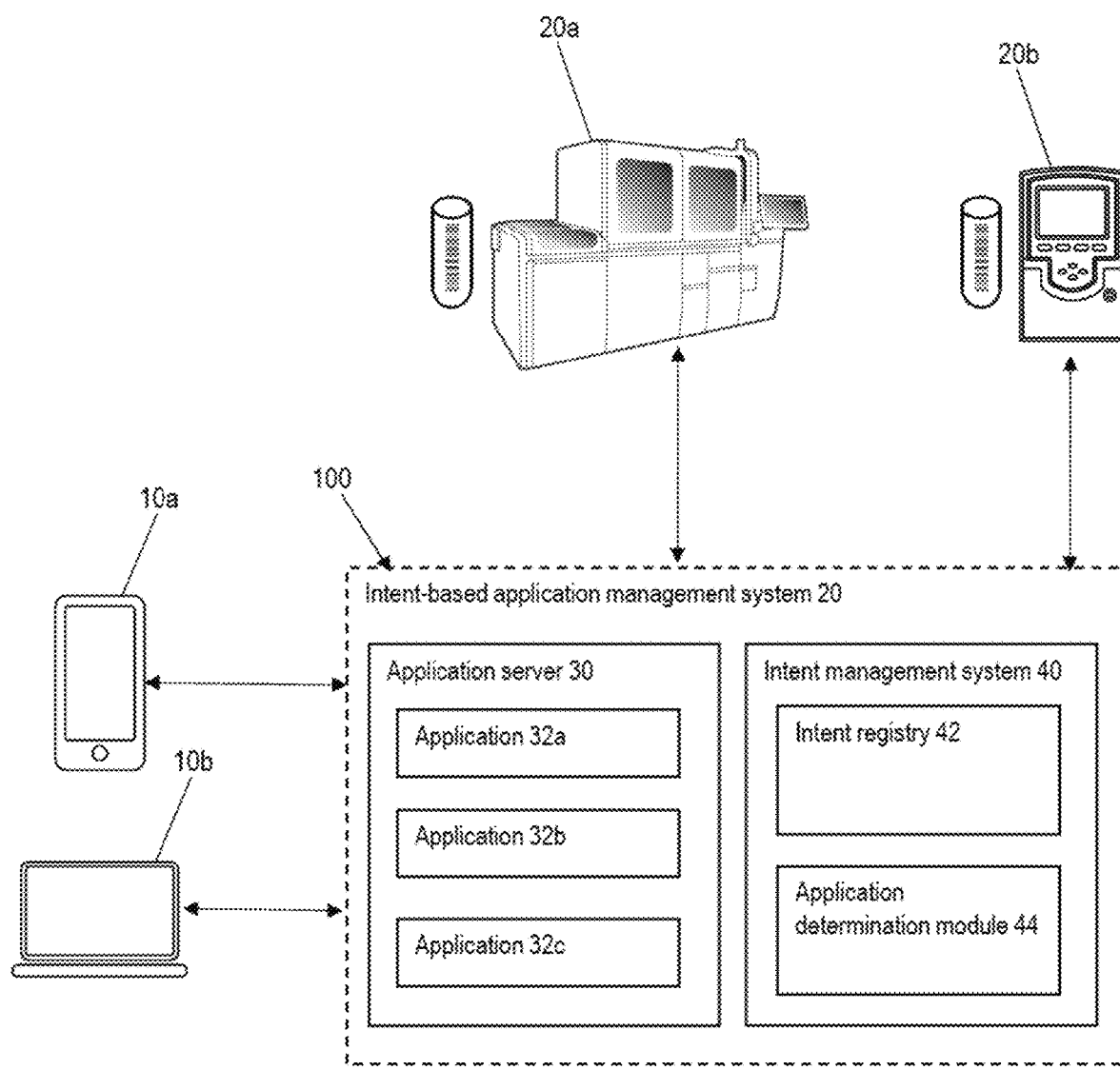
FIG. 1 illustrates a healthcare data management system including or connected to one or more in-vitro diagnostic instruments.

FIG. 1 illustrates an example of a healthcare data management system 100, including or connected to one or more in in-vitro diagnostic instruments, herein abbreviated as "IVD", instruments 60a, 60b for processing biological samples. Instrument 60a is a laboratory based IVD instrument whereas instrument 60b is a point-of-care (POC) IVD instrument.

A biological sample can comprise a biological material, e.g. as taken from a human body or an animal body. A biological sample can comprise a body fluid, such as blood, interstitial fluid, urine, saliva, or other types of body fluids. For simplicity, biologicals samples are herein typically only referred to as "samples".

A sample can potentially comprise at least one analyte of interest, e.g. molecules, ions, proteins, metabolites, pathogens, and the like. It is typically one of the tasks of IVD testing to detect the presence resp. absence and/or a concentration of one or more analytes in a sample. More generically, IVD testing can refer to determining a biological property of a sample. IVD testing can comprise performing at least one analytical test on a sample, wherein the analytical test can allow to draw conclusions on the biological properties of the sample. The analytical test can e.g. comprise adding a reagent to the sample, a possible detectable reaction of the sample with the reagent, and/or a detecting or non-detection of this reaction. Detecting of an reaction can e.g. comprise measuring a physical value of the sample (resp. a composite obtained by using the sample such as a sample-reagent mixture), such as a spectrum and/or an intensity of a radiation reflected by and/or transmitted through the sample (resp. the composite obtained by using the sample).

Processing a sample can e.g. comprise transporting the sample (typically in IVD containers such as IVD tubes; the IVD containers may be held in IVD container holders such as IVD tube racks), performing pre-analytical steps on the samples (e.g. preparatory steps such as centrifuging), performing analytical steps on the samples (e.g. adding a reagent to the sample and measuring the reaction of the sample with the reagent), and/or performing post-analytical steps on the samples (e.g. storing of a sample in a refrigerator for later use).

The IVD instruments 60a,b are designed for processing samples, e.g. for performing one or more steps of an intended workflow on the sample. Processing a sample can comprise one or more physical processing steps (e.g. moving, mixing, heating, etc.). An IVD instruments 60a,b can comprise instrument hardware for processing samples (e.g. gripper, reagent storage, pipetting apparatus, heating element, etc.) as well as instrument software designed for operating the instrument hardware. An IVD instrument 60a,b can comprise a control unit designed for controlling, in particular steering, the operation of the instrument hardware, wherein the instrument software can be designed for being executed using the control unit.

The IVD laboratory instrument 60a may be categorized according to the different type of sample processing steps it can perform. A transport IVD laboratory instrument is designed for transporting samples (resp. the IVD containers and/or respective holders), e.g. from one IVD laboratory instrument to another. A pre-analytical IVD laboratory instruments is designed for performing pre-analytical steps on the samples. A analytical IVD laboratory instrument is designed for performing analytical steps (such as an analytical test) on the samples; an analytical IVD laboratory instrument can comprise a digital analytical IVD laboratory instrument designed for performing analytical computation steps (e.g. a medical algorithm). A post-analytical IVD laboratory instrument is designed for performing post-analytical steps on the samples. Some IVD instruments 60a,b are capable of performing multiple type of sample processing steps, e.g. pre-analytical and analytical steps.

The IVD instruments 60a,60b are connected to an intent-based application management system 20 discussed in detail below. They exchange data bidirectionally with the intent-based application management system 20, The data can include, for example, IVD data (e.g. medically relevant data such as blood glucose level) and instrument data (e.g. operating data such as reagent level). The intent-based application management system 20 is also connected to one or more client devices such as a smartphone 10a or a laptop computer 10b. Generally, the IVD instruments 60a,60b can be considered as sources of data which the client devices 10a,10b may wish to access via the intent-based application management system 20. However, it should be noted that the IVD instruments themselves can be client devices i.e. requesting the use of the intent-based application management system 20. Moreover, the IVD instruments may be given instructions or commands via applications managed by the intent-based application management system e.g. via intents executed using a (or another) client device.

Figure 2:
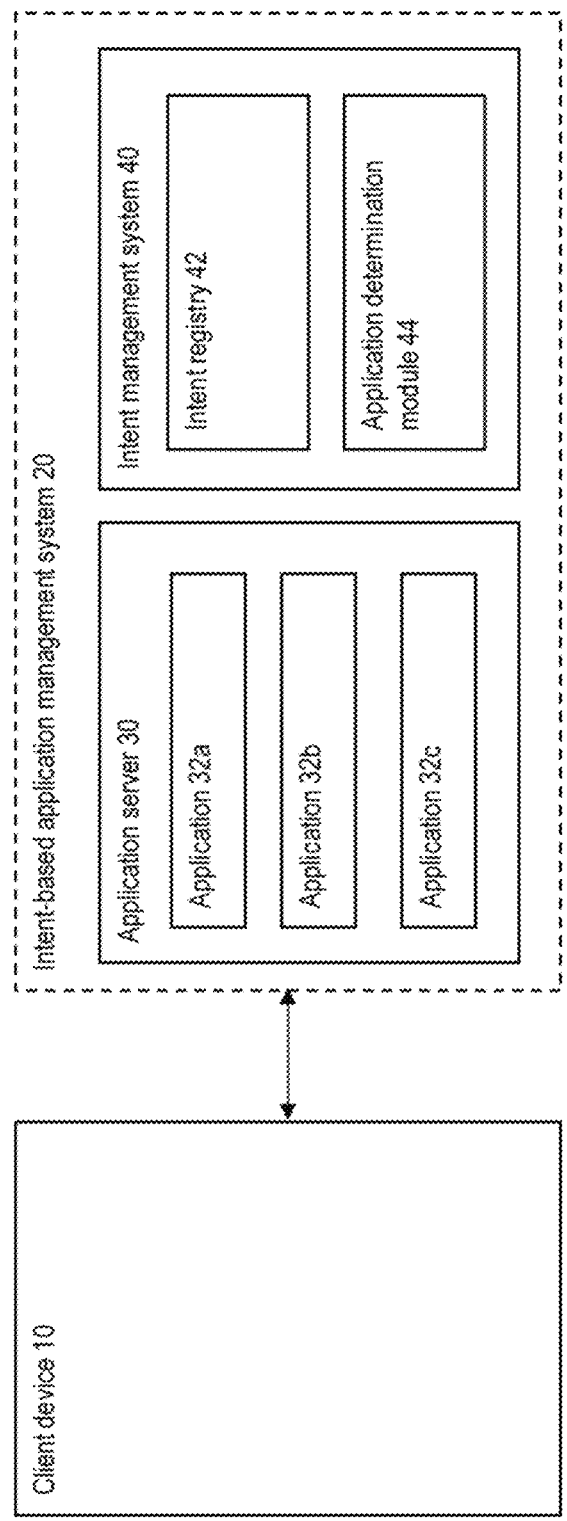
FIG. 2 shows a high-level system diagram illustrating features of the present disclosure.

FIG. 2 shows a high-level system diagram illustrating the features of the present disclosure. Specifically, FIG. 2 shows an intent-based application management system 20 which is connected to a client device 10. The means by which the two are connected is not shown in FIG. 2, so it should be understood that the client device 10 may be connected to the intent-based application management system 20 in any way (discussed later in this application). It should be appreciated that in some cases, the client device 10 may be part of the intent-based application management system 20 itself. The intent-based application management system 20 includes an application server 30 hosting applications 32a, 32b, 32c, and intent management system 40, which includes at least intent registry 42 and application determination module 44.

In use, a user of the client device 10 sends an intent to the intent-based application management system 20. Then, the application determination unit 44 performs a lookup in the intent registry 42 to determine which of the applications 32a, 32b, 32c are suitable to execute the specific operation associated with the received intent. Examples of tables which may be included in the intent registry 42 is shown in FIGS. 3A and 3B. Note that FIGS. 3A and 3B show only an example of an intent registry 42 which may be used.

The intent registry 42 shown in FIG. 3A is in the form of a table having three columns: an intent type ID column, an intent type column, and a column including the applications which are able to execute operations associated with that intent type. It should be noted that even though the data in FIG. 2A are presented as a table, ordered by the intent type ID, the data in the intent registry 42 may not be stored in table form, but may be stored in any structural form in which relationships and/or associations between intent type IDs, intent types, and supporting applications may be established. FIG. 3B shows an alternative table which is representative of the same information as FIG. 3A, except that in FIG. 3B, the data is sorted by application ID, rather than by intent type ID.

FIGS. 2 to 3B illustrate the disclosure in broad terms, but as is clear from the preceding sections of this application, there system may include various additional function modules. Such an arrangement is shown in FIG. 4. the system of FIG. 4 is now described, before explaining, with reference to the subsequent drawings, the functions of the constituent components.

Figure 4:
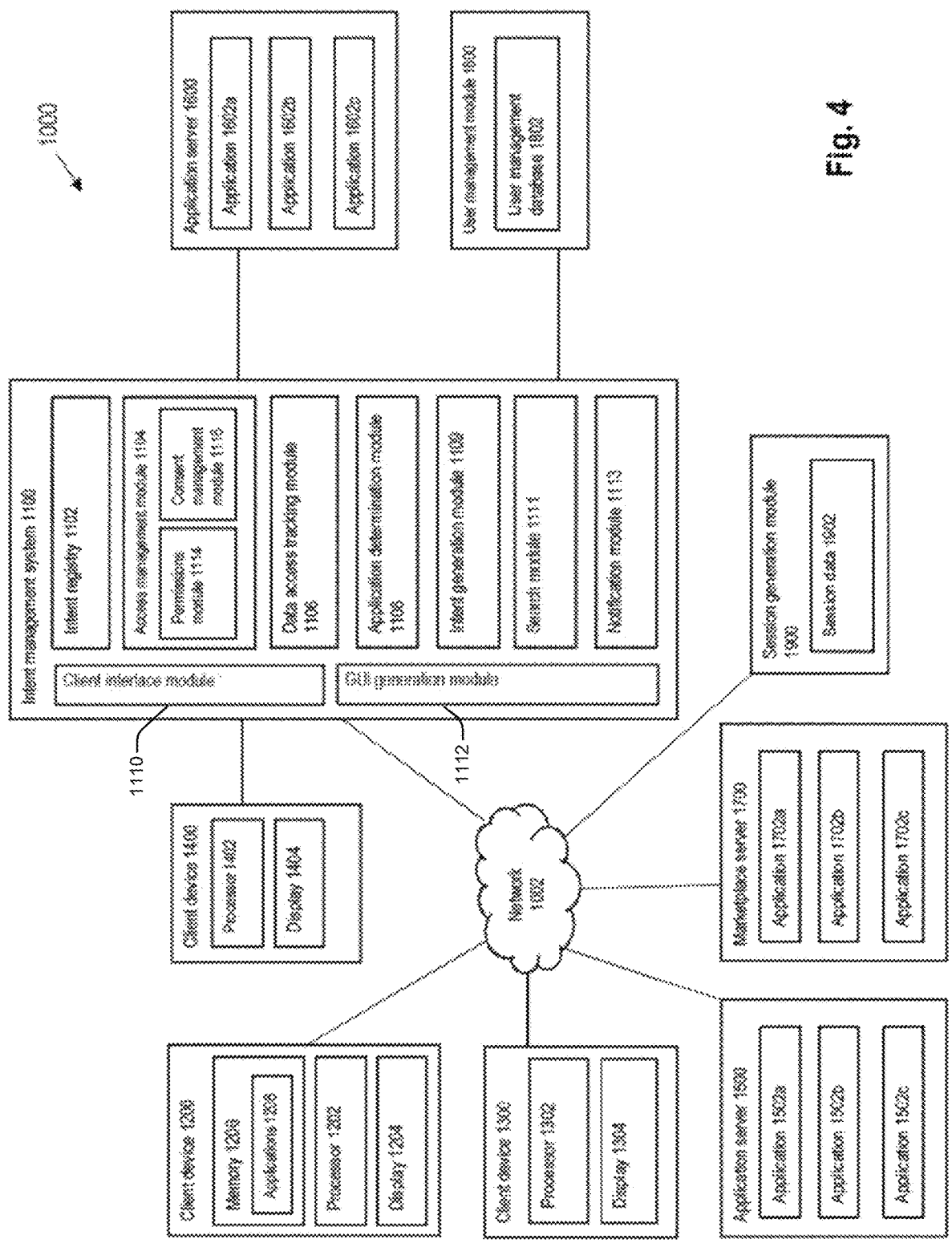
FIG. 4 shows a more detailed system diagram illustrating figures of the present disclosure.

The intent-based application management system 1000 of FIG. 4 includes intent management system 1100, client devices 1200, 1300, 1400, application servers 1500, 1600, 1700 and a user management module 1800 (which may, in some examples, be part of the intent management system 1100). In the example of FIG. 4, the application server 1700 is a marketplace server 1700. It should be noted that the intent management system 1100 could be connected to any number of application servers or client devices, in any number of different ways. The intent management system 1100 is connected to application server 1500, marketplace server 1700, and client devices 1200, 1300 via network 1002, and is connected directly (e.g. via a wired connection) to client device 1400 and application server 1600. Network 1002 may be a wireless network such as a Wi-Fi network, or a cellular network, or a wired network such as a local area network (LAN) or wide area network (WAN). In alternative arrangements, the client devices 1200, 1300, the application server 1500, and the marketplace server 1700 may not all be connected to the intent management system 1100 via the same network, 1002. They may each be connected to the intent management system 1100 by a respective network. One network may be used to connect more than one of the components to the intent management system 1100.

The intent management system 1100 includes an intent registry 1102, an access management module 1104, a data access tracking module 1106, an application determination module 1108, an intent generation module 1109, a client interface module 1110, and a GUI generation module 1112. Of these, the access management module includes a permissions module 1114, and a consent management module 1116. It will be appreciated that the intent management system 1110 may include the permissions module 1114 and the consent management module 1116 independently, i.e. without an access management module.

Client device 1200 includes a memory 1206, a processor 1202, and a display 1204. The memory 1206 includes a plurality of applications 1208. In this respect, in some cases, the client device 1200 may serve as an application server, i.e. the intent management system 1100 may be configured to manage the applications 1208 which are stored in the memory 1206 of the client device 1200. These applications 1208 which are present on the client device 1200 may be referred to herein as "native applications". Users of client device 1200 may be able to use those native applications 1208 to execute desired operations using the processes described throughout this application. Client device 1300 includes a processor 1302 and a display 1304. It should be noted that it may also include a memory and applications, but these are omitted from FIG. 4 since in the present example, any native applications on the client device 1300 are not accessible/managed by the intent management system 1100. As was discussed previously, the client devices may be smartphones, laptop computers, desktop computers, etc. However, the client devices can also include IVD instruments such as IVD laboratory instrument 20a or IVD POC instrument 20b. The client devices can also include healthcare information systems (HIS), laboratory information systems (LIS), electronic medical records (EMRs) and/or third party application systems.

Application server 1500 includes applications 1502a, 1502b, 1502c, and marketplace server 1700 includes applications 1702a, 1702b, 1702c. It will of course be appreciated that the disclosure is not limited to servers containing three applications only.

The client devices 1200, 1300, the application server 1500, and the marketplace server 1700 may each include a respective network interface module which facilitates the connection of that component with the network 1002. The same is true of the intent management system 1100.

Client device 1400 includes processor 1402 and display 1404. Application server 1600 includes applications 1602a, 1602b, 1602c.

The user management module 1800 includes a user management database 1802. In FIG. 4, the user management module 1800 is shown as being directly connected to the intent management system 1100, but it may also be connected to it via the network 1002. Alternatively, the user management module 1800 may be part of the intent management system 1100.

The operation of the intent-based application management system 1000 is now described in generic terms, before describing some use cases in detail. It should be noted that the disclosure of this part of the application may be combined with any element of the disclosure in the "summary of the disclosure" section, where compatible.

In order for the process of the disclosure to begin, it is necessary for an intent to be generated and received by the intent management system 1100. In one example workflow, this may be achieved as follows. Any one of the client devices 1200, 1300, 1400 may have installed thereon a computer program or other software application which enables it to access the intent management system 1100. The computer program or software application may be a portal-, or platform-style application. A user of the client device 1200, 1300, 1400 may use this application to access the intent-based application management system of the present disclosure.

On opening the application, the user may be prompted to log in using their credentials, and a session generation module 1900 may be configured to generate a session, as described earlier in the application. The generated session is associated with a specific user. Information pertaining to all of the users who are able to access the system is stored in the user management database 1800. The session generation module 1900 may include session data 1902 which stores data about e.g. the current session, and optionally further data relating to a session history.

The GUI generation module 1112 may then be configured to generate instructions, and send them to the client device 1200, 1300, 1400, the instructions configured to cause the processor 1202, 1302, 1402 of the client device 1202, 1302, 1402 to render a GUI on the display 1204, 1304, 1404 of the client device 1200, 1300, 1400. The generated GUI may include an input receiving object. The user may then provide some kind of input to the input receiving object (e.g. by typing text into the object, or by clicking a hyperlink associated with the input receiving object). The input is received by the client interface module 1110 of the intent management system. In some cases, the input may include an intent. Alternatively, in response to the receipt of the input by the client interface module 1110, the intent generation module 1108 may be configured to generate an input based on the user's input.

Among other things, the intent may specify an OPERATION to be executed, and one or more pieces of DATA (herein, "data items") on which the operation is to be executed. Other optional features of the intent are described elsewhere in this application.

Once the intent has been generated, the application determination module 1108 performs a lookup in the intent registry 1102 to determine which applications of the plurality of application (stored in various places) are able to execute the operation associated with the intent. Consider the scenario where the appropriate applications are 1502a, 1602a, and 1702a. In this case, the application determination module 1108 would identify these applications. The GUI generation module 1112 would then generate instructions which, when received by the client device, cause it to display a supplementary input receiving object. The user is then able to select which of the applications they wish to use to execute the operation. In the case where the user wishes to use application 1702a, when the user indicates this, e.g. by clicking a link to that application 1702a, rather than e.g. the application opening, because it is on the marketplace server 1700 (which is essentially a repository from which applications may be obtained), the user may then be taken to e.g. a website where they are able to download or otherwise access application 1702a. Alternatively, if the application determination module 1108 is able to identify one or more applications to which the user already has access, then the option of the application 1702a on the marketplace server 1700 may not be displayed. Correspondingly, in the case where the user does not yet have access to any suitable applications, the only option for the user may be to acquire an application from the marketplace server 1700.

The next sequence of steps may happen in various different orders, as discussed earlier in this application. Specifically, these steps include the permissions management, and consent management processes, and may slot into the method performed by the system as described above. It is clear from the description below where these permissions management and consent management steps may be performed. As discussed, permissions management relates to determining whether a client device, or a user thereof, is permitted to execute the operation which is associated with an intent received from that client device or user thereof, based on rules associated with e.g. persona or geographic locations. Consent management involves determining whether a subject of a data item has explicitly consented to a resource being accessed by another party.

Figure 5:
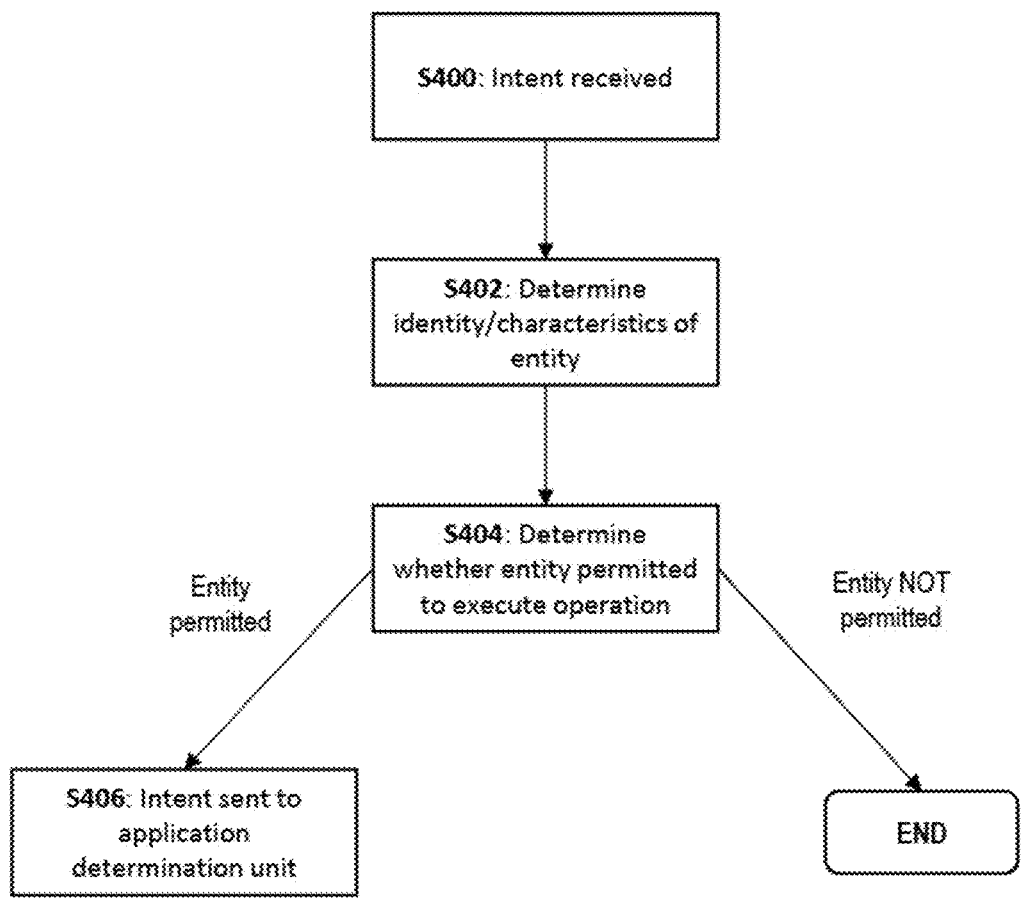
FIG. 5 shows an example of a permission management process.

FIG. 5 shows an example of a permission management process. It will be noted that variations on this method are still covered by the disclosure, such as those set out in detail earlier in this application. In step S400, an intent is received at the client interface module 1114, whereupon it is transmitted to the permissions module 1114 of the access management module 1104. Then in step S402, the permissions module 1114 is configured to determine the identity and/or characteristics of the entity (used herein to refer to the client device 1200, 1300, 1400, or the user thereof). This may be achieved by the permissions module 1114 sending a request to the session generation module 1900, which is able to retrieve the identity of the entity from the session data 1902. The permissions module 1114 may then request additional information about the entity from the user management module 1800 which may be able to retrieve it from the user management database 1802. In step S404 the permissions module 1114 determines whether the entity is permitted to execute the operation associated with the received intent. In order to do so, the permissions module 1114 may perform a lookup in a permissions table. As has already been discussed, permissions data may not be stored in the form of a table, but rather in the form of a data structure comprising nodes and edges which represent data and associations between the data. However, it is convenient to illustrate this in the form of lookup tables. FIGS. 6A to 6E show non-exhaustive examples of permissions tables containing permissions data:

In FIG. 6A a first column of the table lists the various entity IDs, and a second column of the table lists, for each entity ID, the intent type IDs the operations associated with which that entity is permitted to execute. Alternatively, the entity ID could refer to e.g. a class of entity (e.g. based on a persona, a role, or an organization), or a characteristic of the entity (e.g. a security clearance level, a geographical location, or an organization to which that entity belongs).

In FIG. 6B a first column of the table lists the various entity IDs, and a second column lists for each entity ID, one or more operations (i.e. those operations which may be specified in the OPERATION field of an intent) which the entity is permitted to execute. Alternatively, the column may list operation IDs corresponding to those operations, or may otherwise reference the operations. As before, the entity ID could refer to a class of entity, rather than a single entity.

In FIG. 6C a first column of the table lists the various entity IDs, and a second column of the table lists, for each entity ID, one or more data types (i.e. the types of data which may be specified in the TYPE field of an intent) on which the entity is permitted to execute an operation. Alternatively, the column may list type IDs corresponding to those data types, or may otherwise reference the data types. Again, the entity ID could refer to a class of entity, rather than a single entity.

In FIG. 6D a first column of the table lists the various entity IDs, and a second column of the table lists, for each entity ID, one or more specific data items (i.e. the data items which may be specified in the DATA field of the intent) on which the entity is permitted to execute an operation. The second column may specify a specific address of the permitted data items, or otherwise reference them. It will be appreciated that this is the most restrictive access control. Once again, the entity ID could refer to a class of entity, rather than a single entity.

In FIG. 6E, a first column of the table lists various entity IDs, and a second column of the table lists, for each entity ID, one or more specific application IDs (i.e. the applications which may be specified in the intent) the entity is permitted to use to excite an operation. The second column may specify a specific application hosted on a specific application server, or may specify an application without indicating the application server (whereupon the system will search to determine the application server hosting the application). Once again, the entity ID could refer to a class of entity rather than a single entity.

In FIGS. 6A to 6E, the lookup tables are shown sorted by entity ID. However, it is possible that the tables be sorted by the feature of the second column instead, and all permitted entities are listed alongside each intent type ID, operation, data type or specific data item. This may be implemented straightforwardly if the data is stored in a structure containing nodes and edges as described above.

After step S404, it is determined whether the entity from whom the intent was received is permitted to execute the operation associated with the received intent. If the entity is permitted to execute the operation, then the permissions module 1114 sends the intent to the application determination unit 1108 and an application is selected as outlined previously with respect to S406. In the entity IS NOT permitted to execute the operation, the process ends. Optionally, the permissions module 1114 may send a request to the GUI generation module 1112 to generate an error message or the like, informing the user of the client device 1200, 1300, 1400 that they do not have permission to execute the requested operation.

Figure 7:
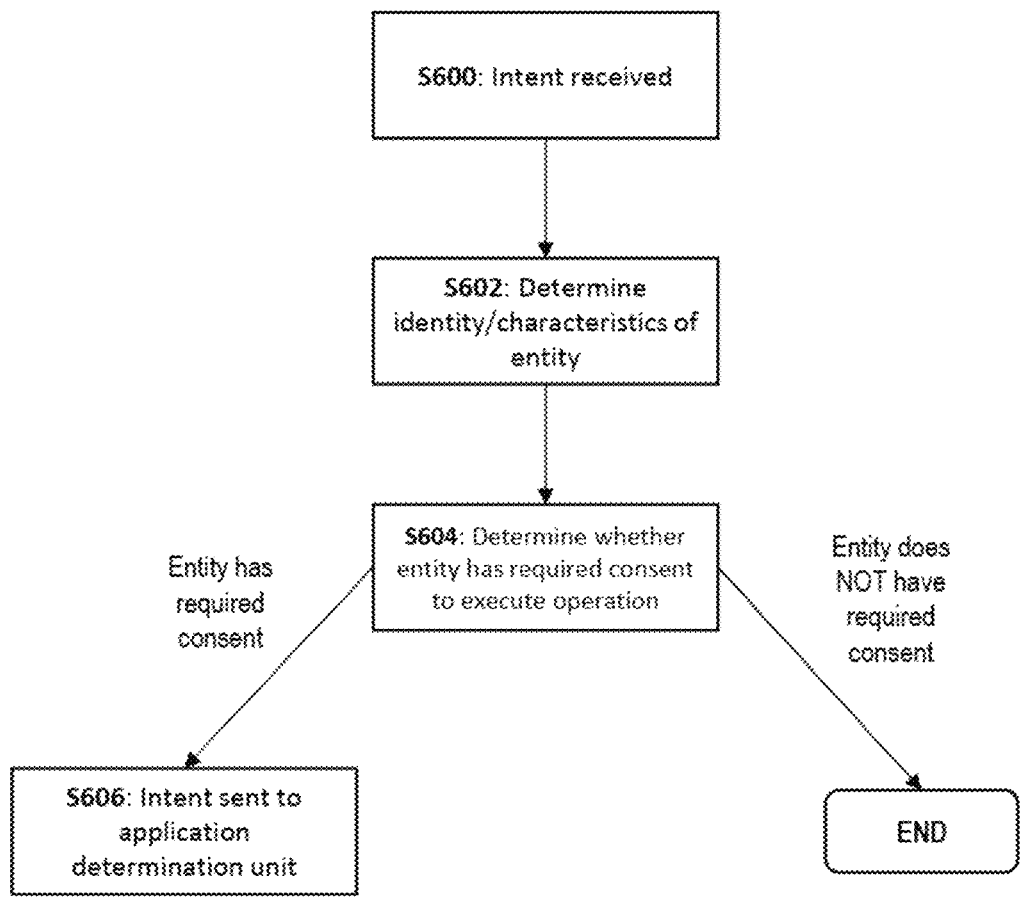
FIG. 7 shows an example of a consent management process.

The overall process may include an additional (or in some cases, alternative) permissions management step in which, after the application determination unit 1108 has determined one or more applications e.g. 1602a, 1602b, 1602c, which are able to execute the operation associated with the received intent, the permissions module 1114 determines whether the entity is permitted to execute operations using each respective application e.g. 1602a, 1602b, 1602c. An example of a further permissions table which may be used for this purpose is shown in FIG. 7. In this table, the first column lists the various entity IDs, and the second column lists the applications which that entity is permitted to use in order to execute an operation associated with an intent. The table may further include the location of the applications (i.e. the identity of the application server on which the application is hosted).

Consent management is now considered, which is handled by the consent management module 1116 of FIG. 4. The process is similar to the permissions management. FIG. 7 shows an example of a consent management process. As before, it will be noted that the variations on this method are still covered by the disclosure, such as those set out in detail earlier in this application. In step S600, an intent is received at the client interface module 1114, whereupon it is transmitted to the consent management module 1116 of the access management module 1104. Then in step S602, the consent management module 1116 is configured to determine the identity and/or characteristics of the entity (used herein to refer to the client device 1200, 1300, 1400, or the user thereof). This may be achieved by the consent management module 1116 sending a request to the session generation module 1900, which is able to retrieve the identity of the entity from the session data 1902. The permissions module 1114 may then request additional information about the entity from the user management module 1800 which may be able to retrieve it from the user management database 1802. In the case of consent management, the additional information may include e.g. a persona of the entity (e.g. whether they are a doctor, a nurse, or hospital technician), or a geographical location of the entity (to ensure that e.g. in the case where a patient consents that their data may only be accessed in a particular country, or in a particular region). In step S604 the consent management module 1116 determines whether the entity is permitted to execute the operation associated with the received intent. As explained previously, in the case of consent management, the operation in question usually relates to accessing a given data item or collection of data items, which may make up e.g. a medical record, so the OPERATION associated with the intent is usually some kind of content retrieval operation.

In the previous example, which related to permissions management, the determination whether a given entity was permitted to execute an operation associated with the intent in question was performed by the permissions module 1114 performing a lookup in a permissions table. Note that this may also be the case for consent management operations. Specifically, the kinds of lookup table which are shown in FIGS. 6C and 6D could also be used for consent management, since they set out, respectively, data types and data items which each a given entity (or class of entity) is permitted to access. In other cases, each data item (or collection of data items) may include, or have associated therewith, consent metadata. This consent metadata may include information relating to entities or classes of entities who are permitted to access that data item. The consent metadata could be in the form of a flag which is stored alongside the data items in question, and may include a list of entities or classes of entities who are permitted to access that data item. In such cases, in step S604, the consent management module 1116 may be configured to retrieve or otherwise access the consent metadata associated with the data item or data items which form the subject of the operation associated with the received intent. Then, the consent management module 1116 may be configured to verify that the consent metadata specifies that the entity (or the corresponding class of entities) is permitted to access the data item or data items. Alternatively, the consent management module 1116 may be configured to determine, based on the consent metadata, which entities or classes of entities are permitted to access the data item in question, and then to verify whether the current entity (or the class of entity to which it belongs) is one of the permitted entities or classes of entities. Considered another way, consent management according to the present disclosure may be thought of as a mix between permissions management and validation against formalized authorization from the user, data owner, and the data source (for example: a lab technician, a laboratory organisation, and a patient). Consents require the acceptance of specific conditions and/or contracts, whereas permissions may be considered simply a binary flag assignment. Both integrate with each other in the system herein, as soon as the consent is accepted or rejected.

After step S604, it is determined whether the entity from whom the intent was received is permitted (i.e. has consent to) to execute the operation associated with the received intent. If the entity IS permitted, that is it does have consent to execute the operation, then the consent management module 1116 is configured to send the intent to the application determination unit 1108 and an application is selected as outlined previously. In the entity IS NOT permitted to execute the operation, the process ends. Optionally, the consent management module 1116 may send a request to the GUI generation module 1112 to generate an error message or the like, informing the user of the client device 1200, 1300, 1400 that they do not have the required consent to execute the requested operation. In some cases, the entity may have "partial consent" to access a group of data items (e.g. the entity may have the requisite consent to access a first subset of the data items, but not have the requisite consent to access a second subset of the data items). In such cases, the process set out earlier in this application (under CASE (II)) may take place. This process is not repeated here.

Figures 8A, 8B:
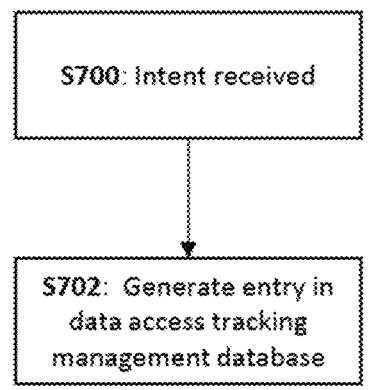
FIG. 8A shows an example of a process by which tracking data may be generated.
FIG. 8B shows an example of an entry in the data access tracking management database.

The data access tracking module 1106 is now discussed, which is used to keep a detailed record of who has request to access which data items, and also whether those requests are successful or unsuccessful. This is particular important when the disclosure is deployed in a healthcare environment, where access to patients' medical documentation must be strictly policed. The flowchart in FIG. 8A shows an example process by which tracking data may be generated by the data access tracking module 1106. In step S700, an intent is received at the client interface module 1110 of the intent management system 1100. Then, in step S702, the data access tracking module 1106 generates an entry in a data access tracking management database, which may form part of the data access tracking module 1106. An example of an entry in the data access tracking database may include, for example, the identity of the user (or client device) from whom the intent was received, information identifying the one or more data items on which the specific operations associated with the intent is to be executed. It has been explained previously that in some cases, because, for example, the user does not have the requisite consent or permission to execute a given operation on a specific data item, the operation may not actually be executed. In those cases, the entry in the data access tracking management database may specify that the user's attempt was unsuccessful. A non-limiting schematic example of an entry 700 in the data access tracking management database is shown in FIG. 8B. The entry 700 includes a plurality of fields including: a user ID field 702, a plurality of fields 704 corresponding to the intent, including an operation field 706, and a data item field 708. The entry 700 also includes a field 710 indicating whether the user's intent was successful (i.e. whether the specific operation associated with the intent was actually executed). The entry 700 also includes a timestamp 712. It should be noted that FIG. 8B is only a schematic representation of an entry 700 in the data access tracking management database; in reality, the entry would be stored in the form of code representing the information in the entry 700.

As discussed, the intent-based system of the present disclosure enables an effective implementation of a searching function. This function is controlled by the search module 1111. In FIG. 3A, the search module 1111 is shown as part of the intent management system 1100, but it should be noted that in some cases, the search module 1111 may be a separate module from the intent management system 1100. FIG. 9A shows an example of a searching process. In step S800, a search query is received. This may be received at an input-receiving objection of a GUI. Next, in step S802, the intent generation module 1109 generates a search intent based on the search input. In some cases, a query generation module may generate a formal search query based on the search input, and the intent generation module 1109 may generate the search intent based on the generated formal search query. A detailed description of the search intent is set out earlier in this application and isn't repeated here. Three types of data may be searched: user information in the user management database 1802, information collected from the portal (which may include e.g. notifications and events which are logged), and crucially data provided by the applications to which the user has access. In step S802, the search module 1111 generates search results based on the search intent. FIGS. 9B, and 9C illustrate different ways in which the search results may be generated:

In FIG. 9B, in step S802a, a search database is generated. The search database comprises data from all of the applications to which a user in question has access. Then in step S802b, the search module 1111 performs a search of the generated search database, to identify data matching the search criteria. As discussed, this method enables the search module 1111 only to have to search a single database.

In FIG. 9C, a different approach is adopted. In step S802a', the search module 1111 generates a respective search request for each of the sources of data which are to be searched (e.g. the user management database, a log of information which is collected from the portal, an the various applications to which the user has access). In step S802b', the search requests (which may be in the form of intents) are transmitted to the various data sources. Then, in step S802c', the search module 1111 receives a plurality of results from the various data sources, the results including the data item or data items which meet the criteria specified in the initial search input. In a similar, alternative, arrangement, the search module 1111 may send the search query or search intent to the intent management system 1100, which itself is configured to generate the search requests, and to transmit them to the respective sources. The intent generation module 1109 may be configured to generate the individual search requests in this case (in the form of intents).

Figures 9D, 9E:
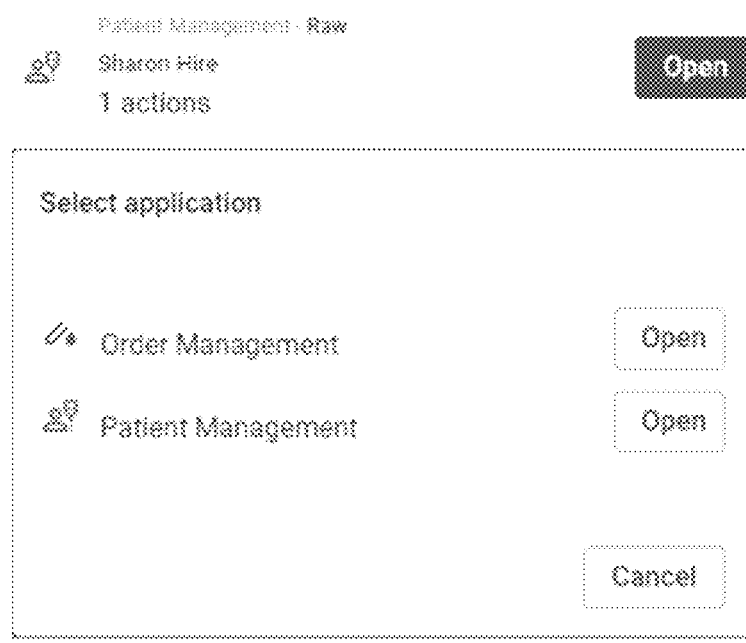
FIG. 9D is a schematic indicating the kind of information which may form the search result.
FIG. 9E shows an example of an intent which may be displayed in the search results.

In step S804, the search results may be displayed. For example, the search module 1111 may transmit them to the GUI generation module 1112, which is then configured to generate instructions which, when executed by a client device 1200, 1300, 1400 causes them to display the search results on a respective display 1204, 1304, 1404. Alternatively, the search module 1111 may send the search results directly to the client device 1200, 1300, 1400. FIG. 9D is a schematic of the kind of information which may form the search result. The information shown in FIG. 9D should not be taken as limiting. Indeed, the search result may omit any one or more of the pieces of information, and may include others in addition to the ones shown. Search result 850 includes the following fields: the source of the search result 852, a date associated with the search result 854, a quality score 856, a match number 858, one or more intents 860. The search module 1111 (or another component) generates the intent 860 associated with the search result 850. The intent 860 may be in the form of a clickable link which causes the intent 860 to be transmitted to the intent management system 1100, to be processed in the usual way. FIG. 9E shows an example of an intent which may be displayed in the search results. It should be noted that only the intent 860 may actually be displayed to the user. The other features (i.e. the source 852, the date 854, the quality score 856, and the match number 858) may not actually be displayed to the user, but may be used, for example, to rank the search results when displayed to the user. In FIG. 9E, having searched for "Sharon Hire" in a patient management database (e.g. in a patient management application), the user is shown that there is one action associated with the search result (i.e. an action which will display Sharon Hire's patient management information). When a user clicks the "Open" link, they are offered a choice of applications which may be used to access the requested information (i.e. the "Order Management" application, and the "Patient Management" application). These links cause already-generated intents to be transmitted to the intent management system 1100 (in this case, the "COMPONENT" field of the intent is specified so that the application is already determined).

Figure 10:
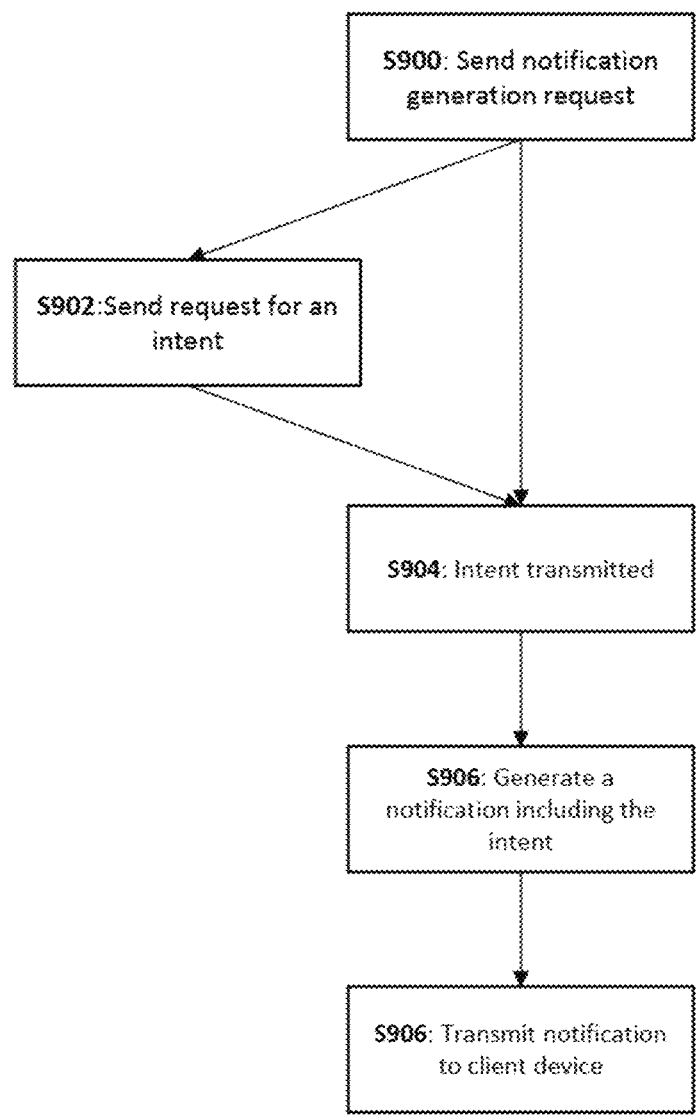
FIG. 10 shows an example of a process by which a notification is generated.

Now discussed is the notification process which may be employed by the present disclosure, and which is illustrated in FIG. 10. The notification process takes place in response to some "event", which should be understood to refer to some action which takes place of which it is desirable to inform a user. For example, an event could refer to an update to a patient's information, or a laboratory machine detecting that the remaining amount of a reagent falls below a predetermined threshold. The event may originate in an application, and in response to the event taking place, in step S900, the application sends a notification generation request to the notification module 1113. To allow the notification module 1113 to generate the notification, the notification generation request may include information about the event, such as the nature of the event, the application from which the event originated, a timestamp. The notification generation request may include an intent which is to be included in the notification. When the notification generation request does not include an intent, in step S902, the notification module 1113 sends a request to the intent generation module 1109. Alternatively, the application may send the intent generation module 1109 the request for an intent. In step S904, the intent may be transmitted back to the notification module 1113, and in step S906, the notification module 1113 generates a notification including the generated intent. In addition, the notification may include other information about the event, e.g. the nature of the event, and any other information required. Once the notification is generated by the notification module 1113, in step S908, the notification (containing the intent) is transmitted to the client device 1200, 1300, 1400. The notification may include instructions which, when received by the client device 1200, 1300, 1400, cause it to display the notification. When the notification is opened, the user may then be presented with the intent (or a plurality thereof) which is then processed in the usual way. An important advantage of this feature of the disclosure is that the operation associated with the intent in the notification need not be executed using the application from which the notification originated.

The systems and methods of the above embodiments may be implemented in a computer system (in particular in computer hardware or in computer software) in addition to the structural components and user interactions described.

The term "computer system" includes the hardware, software and data storage devices for embodying a system or carrying out a method according to the above described embodiments. For example, a computer system may comprise a central processing unit (CPU), input means, output means and data storage. The computer system may have a monitor to provide a visual output display. The data storage may comprise RAM, disk drives or other computer readable media. The computer system may include a plurality of computing devices connected by a network and able to communicate with each other over that network.

The methods of the above embodiments may be provided as computer programs or as computer program products or computer readable media carrying a computer program which is arranged, when run on a computer, to perform the method(s) described above.

The term "computer readable media" includes, without limitation, any non-transitory medium or media which can be read and accessed directly by a computer or computer system. The media can include, but are not limited to, magnetic storage media such as floppy discs, hard disc storage media and magnetic tape; optical storage media such as optical discs or CD-OMs; electrical storage media such as memory, including RAM, ROM and flash memory; and hybrids and combinations of the above such as magnetic/optical storage media.

While the disclosure has been described in conjunction with the exemplary embodiments described above, many equivalent modifications and variations will be apparent to those skilled in the art when given this disclosure. Accordingly, the exemplary embodiments of the disclosure set forth above are considered to be illustrative and not limiting. Various changes to the described embodiments may be made without departing from the spirit and scope of the disclosure.

In particular, although the methods of the above embodiments have been described as being implemented on the systems of the embodiments described, the methods and systems of the present disclosure need not be implemented in conjunction with each other, but can be implemented on alternative systems or using alternative methods respectively.

The features disclosed in the description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the disclosure in diverse forms thereof.

While the disclosure has been described in conjunction with the exemplary embodiments described above, many equivalent modifications and variations will be apparent to those skilled in the art when given this disclosure. Accordingly, the exemplary embodiments of the disclosure set forth above are considered to be illustrative and not limiting. Various changes to the described embodiments may be made without departing from the spirit and scope of the disclosure.

For the avoidance of any doubt, any theoretical explanations provided herein are provided for the purposes of improving the understanding of a reader. The inventors do not wish to be bound by any of these theoretical explanations.

Any section headings used herein are for organizational purposes only and are not to be construed as limiting the subject matter described.

Throughout this specification, including the claims which follow, unless the context requires otherwise, the word "comprise" and "include", and variations such as "comprises", "comprising", and "including" will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means for example +/−10%.

Clauses—1

1. An intent-based application management system, accessible by a plurality of client devices, the system including:
    one or more application servers hosting a plurality of applications, each application configured to execute one or more predetermined operations;
    an intent management system including:
    an intent registry, storing information about a plurality of intents, the information for each intent including:
        an intent type identifier, and
        one or more applications configured to execute an operation associated with the intent type;
    and the intent management system further comprising:
    an application determination module configured to receive an intent, and to determine, using the intent registry, one or more applications configured to execute an operation associated with the received intent.

2. The intent-based application management system of clause 1, wherein the intent includes a plurality of fields, each field containing a respective datum indicating an aspect of and/or parameter associated with the operation to be executed.

3. The intent-based application management system of clause 2, wherein the fields include one or more of:
    an operation field defining the type of operation to be executed; and a data field defining one or more items on which the operation is to be executed.

4. The intent-based application management system of any preceding clause, further comprising:
a client device interface module configured to receive an input from one or more of the client devices.

5. The intent-based application management system of clause 4, further comprising: an intent generation module, configured to generate the intent based on at least the client device input.

6. The intent-based application management system of clause 5, wherein the intent generation module is configured to generate the intent by populating one or more fields of the intent based on at least the client device input.

7. The intent-based application management system of clause 5 or 6, wherein the intent generation module is configured to generate a requirement specification based on properties of the client device and/or the user of the client device from which the input is received.

8. The intent-based application management system of clause 7, wherein the properties of the client device include one or more of:
a make of the client device; a model of the client device; a type of client device; a geographical location of the client device; a status of the client device; and a configuration of the client device.

9. The intent-based application management system of clause 7 or 8, wherein the property of the user of the client device may include one or more of: a persona or role of the user.

10. The intent-based application management system of any preceding clause, further including a graphical user interface, GUI, generation module, configured to generate GUI rendering instructions which, when received by the client device, cause the client device to render a GUI, the GUI including an input receiving object configured to receive user input; and
wherein the intent-based application management system further includes a natural language processing module, configured to identify one or more words in the input; and
an intent registry searching module of the intent-based application management system is configured to identify one or more intents, within the intent registry, related to the or each identified word.

11. The intent-based application management system of any preceding clause, further comprising:
an access control module, configured to determine whether a client device or user of the client device is permitted to execute the operation which is associated with an intent received from that entity by:
determining whether the client device or user of the client device has one or more properties which allow it to execute the operation; and/or
determining whether the execution of the operation requires consent from another party, and then establishing whether consent has been obtained.

12. The intent-based application management system of any preceding clause, further comprising:
a data access tracking module, configured to track the activity of client devices or users of client devices using the application management system.

13. The intent-based application management system of any preceding clause, further comprising a search module, configured to perform a search on data stored by the intent-based application management system to which a user of a client device has access.

14. The intent-based application management system of clause 13, wherein the search module is configured to search a search database, wherein the search database is an internal database of the intent-based application management system which is fed with data collected from one or more of the applications to which the user of the client device has access.

15. The intent-based application management system of either clause 13 or 14, wherein the search module is configured to generate a respective search request for each of a plurality of sources of data, and to transmit the requests to the respective sources.

16. The intent-based application management system of clause 15, wherein the search requests are in the form of intents.

17. The intent-based application management system of any of clauses 13-16, wherein the search module is configured to send a search query or a searching intent, received from the user, to the intent management system, the intent management system being configured to generate one or more search requests and to transmit them to one or more respective sources of data.

18. The intent-based application management system of any of clauses 13-17, wherein the search module is configured to generate a lookup table from data in the intent register, the lookup table containing information regarding applications and whether or not they provide search functionality.

19. The intent-based application management module of any of clauses 13-18, wherein the search module provides search results which include one or more of the following features:
information specifying the source of the respective search result;
a date associated with the respective search result;
a quality scored associated with the respective search result;
a match number, indicating how many of the words in the respective search result match words in a respective search input; and
one or more intents.

20. The intent-based application management system of any preceding clause, further comprising a notification module configured to receive a notification generation request from an application, the notification generation request including an intent to be included in the notification as well as information about the nature of an event about which a user of the client device is to be notified.

21. The intent-based application management system of clause 20, wherein the notification includes an intent.

22. The intent-based application management system of clause 21, wherein when an intent is not received from the application as a part of the notification generation request, the notification module is configured to request that the intent generation module generate an intent and transmits it to the notification module.

23. The intent-based application management system of any of clauses 20-22, wherein the notification module causes the notification including the intent to be displayed on the client device of the user.

24. The intent-based application management system of any of clauses 20-23, wherein the notification further includes one or more of: information about the nature of the event about which the user of the client device is to be notified; the application sending the notification generation request; and the time/date.

25. The intent-based application management system of any of clauses 20-24, wherein the intent provided in the notification causes the application server to provide to the client device a list of one or more applications associated with the intent.

26. The intent-based application management system of any preceding clause, connected to one or more external devices or systems, and configured to receive from the one or more external devices or systems one or more external intents, and to then convert or translate the one or more external intents into corresponding intents applicable within the intent-based application management system.

27. A computer-implemented method of managing intent-based applications, the computer-implemented method including steps of:
receiving an intent;
determining, using an intent registry, one or more applications configured to execute an operation associated with the received intent, wherein:
the intent registry stores information about a plurality of intent types, the information including, for each intent: an intent type identifier, and one or more applications configured to execute an operation associated with the intent type; and
executing the operation associated with the received intent using one or more of the determined operations.

Clauses—2

1. A healthcare data management system for managing healthcare data comprising in-vitro diagnostics, IVD, data created using at least one IVD analytical instrument, the healthcare data management system being accessible by a plurality of client devices, the healthcare data management system including:
a plurality of healthcare applications, each healthcare application being configured to execute one or more predetermined operations associated with the healthcare data management system using healthcare data of the healthcare data management system;
an intent management system including:
an intent registry, storing information about a plurality of intents, the information for each intent including:
an intent type identifier, and one or more healthcare applications configured to execute an operation associated with the intent type;
and the intent management system further comprising:
a healthcare application determination module configured to receive an intent, and to determine, using the intent registry, one or more healthcare applications configured to execute an operation associated with the received intent.

2. The healthcare data management system of clause 1, wherein the intent includes a plurality of fields, each field containing a respective datum indicating an aspect of and/or parameter associated with the operation to be executed.

3. The healthcare data management system of clause 2, wherein the fields include one or more of:
an operation field defining the type of operation to be executed; and
a data field defining one or more items on which the operation is to be executed.

4. The healthcare data management system of any preceding clause, further comprising: a client device interface module configured to receive an input from one or more of the client devices.

5. The healthcare data management system of clause 4, further comprising:
an intent generation module, configured to generate the intent based on at least the client device input.

6. The healthcare data management system of clause 5, wherein the intent generation module is configured to generate the intent by populating one or more fields of the intent based on at least the client device input.

7. The healthcare data management system of clause 5 or 6, wherein the intent generation module is configured to generate a requirement specification based on properties of the client device and/or the user of the client device from which the input is received.

8. The healthcare data management system of clause 7, wherein the properties of the client device include one or more of:
a make of the client device; a model of the client device; a type of client device; a geographical location of the client device; a status of the client device; and a configuration of the client device.

9. The healthcare data management system of clause 7 or 8, wherein the property of the user of the client device may include one or more of: a persona or role of the user.

10. The healthcare data management system of any preceding clause, further including a graphical user interface, GUI, generation module, configured to generate GUI rendering instructions which, when received by the client device, cause the client device to render a GUI, the GUI including an input receiving object configured to receive user input; and
wherein the intent-based application management system further includes a natural language processing module, configured to identify one or more words in the input; and
an intent registry searching module of the intent-based application management system is configured to identify one or more intents related to the or each identified word.

11. The healthcare data management system of any preceding clause, further comprising:
an access control module, configured to determine whether a client device or user of the client device is permitted to execute the operation which is associated with an intent received from that entity by:
determining whether the client device or user of the client device has one or more properties which allow it to execute the operation; and/or determining whether the execution of the operation requires consent from another party, and then establishing whether consent has been obtained.

12. The healthcare data management system of any preceding clause, further comprising: a data access tracking module, configured to track the activity of client devices or users of client devices using the application management system for successful and unsuccessful actions.

13. The healthcare data management system of any preceding clause, further comprising a search module, configured to perform a search on all data stored by the intent-based application management system to which a user of a client device has access.

14. The healthcare data management system of clause 13, wherein the search module is configured to search a search database, wherein the search database is an internal database of the intent-based application management system which is fed with data collected from one or more of the applications to which the user of the client device has access.

15. The healthcare data management system of either clause 13 or 14, wherein the search module is configured to generate a respective search request for each of a plurality of sources of data, and to transmit the requests to the respective sources.

16. The healthcare data management system of clause 15, wherein the search requests are in the form of intents.

17. The healthcare data management system of any of clauses 13-16, wherein the search module is configured to send a search query or a searching intent, received from the user, to the intent management system, the intent management system being configured to generate one or more search requests and to transmit them to one or more respective sources of data.

18. The healthcare data management system of any of clauses 13-17, wherein the search module is configured to generate a lookup table from data in the intent register, the lookup table containing information regarding applications and whether or not they provide search functionality.

19. The healthcare data management module of any of clauses 13-18, wherein the search module provides search results which include one or more of the following features:
   information specifying the source of the respective search result;
   a date associated with the respective search result;
   a quality scored associated with the respective search result;
   a match number, indicating how many of the words in the respective search result match words in a respective search input; and
   one or more intents.

20. The healthcare data management system of any preceding clause, further comprising a notification module configured to receive a notification generation request from an application, the notification generation request including an intent to be included in the notification as well as information about the nature of an event about which a user of the client device is to be notified.

21. The healthcare data management system of clause 20, wherein the notification includes an intent.

22. The healthcare data management system of clause 21, wherein when an intent is not received from the application as a part of the notification generation request, the notification module is configured to request that the intent generation module generate an intent and transmits it to the notification module.

23. The healthcare data management system of any of clauses 20-22, wherein the notification module causes the notification including the intent to be displayed on the client device of the user 24. The healthcare data management system of any of clauses 20-23, wherein the notification further includes one or more of: information about the nature of the event about which the user of the client device is to be notified; the application sending the notification generation request; and the time/date.

25. The healthcare data management system of any of clauses 20-24, wherein the intent provided in the notification causes the application server to provide to the client device a list of one or more applications associated with the intent.

26. The healthcare data management system of any preceding clause, connected to one or more external devices or systems, and configured to receive from the one or more external devices or systems one or more external intents, and to then convert or translate the one or more external intents into corresponding intents applicable within the intent-based application management system.

The invention claimed is:

1. A healthcare data management system for managing electronic healthcare data comprising in-vitro diagnostics (IVD) data created using at least one IVD analytical instrument, the healthcare data management system being accessible by a plurality of client computing devices, the healthcare data management system including:
   a plurality of healthcare applications, each healthcare application being configured to execute one or more operations associated with the healthcare data management system using healthcare data of the healthcare data management system;
   a healthcare data operations management system including:
      a healthcare data operations registry, storing information about a plurality of healthcare data operations, the information for each healthcare data operation including:
         a healthcare data operation type identifier, and
         identification(s) of at least one of the one or more healthcare applications configured to execute an operation associated with healthcare data operation type;
      a healthcare application determination module configured to receive a healthcare data operation request or command, and to determine, based on analysing the request or command and performing a lookup in the healthcare data operations registry, a selection of the one or more healthcare applications configured to execute a healthcare data operation associated with the received data operation request or command, and at least one of reporting the selection or causing the selected one or more healthcare data processing applications to execute the requested or commanded healthcare data operation.

2. The healthcare data management system of claim 1, further comprising:
   a client device interface module configured to receive an input and/or properties from the use of one or more of the client devices;
   an intent generation module configured to translate the input and/or properties of the use of the one or more client devices to the healthcare application determination module as the healthcare data operation request or command.

3. The healthcare data management system of claim 2, wherein the intent generation module is configured to generate a requirement specification for a healthcare data operation based on properties of the client device and/or a user account from which the input is received.

4. The healthcare data management system of claim 3, wherein the property of the user of the client device may include one or more of: a digital profile or operational role of the user account.

5. The healthcare data management system of claim 1, further including a graphical user interface (GUI) generation module, configured to generate GUI-rendering instructions which, when received by the client device, cause the client device to render a GUI, the GUI including an input receiving interface configured to receive user input; and
   wherein the healthcare data operations management system further includes a natural language processing module, configured to identify one or more words based on the received user input, wherein performing the lookup in the healthcare data operations registry is based on the identifying of the word(s); and
   a healthcare data operations registry searching module of the healthcare application management system that is configured to identify one or more healthcare data operations related to the identified word(s).

6. The healthcare data management system of claim 1, further comprising:
an access control module, configured to determine whether a client device or user of the client device is permitted to execute the healthcare data operation which is associated with an input received from the client device by:
determining whether the client device or user of the client device has one or more properties which allow it to execute the operation; and/or
determining whether the execution of the operation requires consent from another party, and then establishing whether consent has been obtained.

7. The healthcare data management system of claim 6, further comprising:
a data access tracking module, configured to track the activity of client devices or user accounts using the application management system and access control module for successful and unsuccessful actions and used to generate a report of the successful and unsuccessful actions.

8. The healthcare data management system of claim 6, further comprising a healthcare data search module, configured to perform a search on healthcare data accessible by the healthcare data operations management system based on which a user or a client device has access as determined by the access control module, the search associated with the execution of the healthcare data operation associated with the received data operation request or command.

9. The healthcare data management system of claim 1, further comprising a notification module configured to receive a notification generation request associated with the data operation request or command, the notification generation request comprising information about the type of an event about which a user of the client device is to be notified, and to cause the generation of a notification on the client device in response to the type of event occurring with respect to the data operation request or command.

10. The healthcare data management system of claim 1, connected to one or more external devices or systems, and configured to receive from the one or more external devices or systems one or more external requests or commands and/or properties of the one or more external devices, and to then convert or translate the one or more external requests or commands and/or properties into corresponding healthcare data operation requests or commands applicable within the healthcare data operations management system.

11. A computer implemented method of processing electronic healthcare data comprising in-vitro diagnostics (IVD) data created using at least one IVD analytical instrument, the method comprising:
storing information in a healthcare data operations registry, the information for each healthcare data operation including:
a healthcare data operation type identifier, and
identification(s) of one or more healthcare applications configured to execute an operation associated with healthcare data operation type;
receiving a request or command to perform a healthcare data operation from at least one of a plurality of client computing devices;
selecting, from the one or more healthcare applications, healthcare application(s) to execute a healthcare data operation associated with the received data operation request or command, the selecting based on analysing the request or command and performing a lookup in the healthcare data operations registry;
at least one of causing a display of the selection or causing the selected one or more healthcare data processing applications to execute the requested or commanded healthcare data operation.

12. The method of claim 11 further comprising:
receiving an input at from one or more of the client devices;
at an intent generation module, communicating the input from the one or more client devices to a healthcare application determination module as the healthcare data operation request or command.

13. The method of claim 12 comprising, at the intent generation module, generating a requirement specification for a healthcare data operation based on properties of the client device and/or a user account from which the input is received.

14. The method of claim 13, wherein the property of the user of the client device may include one or more of: a digital profile or operational role of the user account.

15. The method of claim 11 further comprising the generation of a graphical user interface (GUI) to receive the input from a user;
processing the input using a natural language processing module to identify one or more words based on the received user input, wherein performing the lookup in the healthcare data operations registry is based on the identifying of the word(s).

16. The method of claim 11 further comprising:
determining, at an access control module, whether a client device or user of the client device is permitted to execute the healthcare data operation which is associated with an input received from that client device by:
determining whether the client device or user of the client device has one or more credentials which allow the client device to cause execution of the operation; and/or
determining whether the execution of the operation requires consent from another party, and then establishing whether consent has been obtained.

17. The method of claim 16 further comprising tracking the activity of client devices or user accounts using the application management system and an access control module for successful and unsuccessful actions and generating a report of the successful and unsuccessful actions.

18. The method of claim 16 further comprising performing a search on electronic healthcare data based on the data operation request or command and the determining of whether the client device or user of the client device has the one or more credentials or required consent to allow the client device to cause execution of the operation.

19. The method of claim 11 further comprising receiving a notification generation request associated with the data operation request or command, the notification generation request comprising information about the type of an event about which a user of the client device is to be notified, and causing the generation of a notification on the client device in response to the type of event occurring with respect to the data operation request or command.

20. The method of claim 11 further comprising receiving from a plurality of one or more external devices or systems one or more external requests or commands and/or properties of the external devices or systems, and to then convert or translate the one or more external requests or commands and/or properties of the external devices or systems into corresponding healthcare data operation requests or commands applicable within the healthcare data operations management system.

\* \* \* \* \*